(12) United States Patent
Hitzeman et al.

(10) Patent No.: US 6,670,154 B1
(45) Date of Patent: Dec. 30, 2003

(54) AUTOMATIC EUKARYOTIC ARTIFICIAL CHROMOSOME VECTOR

(76) Inventors: Ronald A. Hitzeman, 15 Banff Way, Pacifica, CA (US) 94044; George E. Chisholm, IV, 864 Overlook Ct., San Mateo, CA (US) 94403

( * ) Notice: Subject to any disclaimer, the term of this patent is extended or adjusted under 35 U.S.C. 154(b) by 0 days.

(21) Appl. No.: 09/744,732

(22) PCT Filed: Jul. 26, 1999

(86) PCT No.: PCT/US99/16297

§ 371 (c)(1),
(2), (4) Date: Jan. 26, 2001

(87) PCT Pub. No.: WO00/06715

PCT Pub. Date: Feb. 10, 2000

Related U.S. Application Data
(60) Provisional application No. 60/094,294, filed on Jul. 27, 1998.

(51) Int. Cl.$^7$ .................... C12N 15/64; C12N 15/03; C12N 15/63; C12N 15/85

(52) U.S. Cl. ................ 435/91.42; 435/320.1; 435/454

(58) Field of Search .................. 435/320.1, 454, 435/91.42

(56) References Cited

U.S. PATENT DOCUMENTS

| | | | |
|---|---|---|---|
| 4,889,806 A | 12/1989 | Olson et al. | |
| 5,248,605 A | 9/1993 | Chatterjee | |
| 5,288,625 A | 2/1994 | Hadlaczky | |
| 5,334,526 A | 8/1994 | Smith et al. | |
| 5,474,896 A | 12/1995 | Dujon et al. | |
| 5,721,118 A | 2/1998 | Scheffler | |
| 6,265,211 B1 * | 7/2001 | Choo et al. | 435/320.1 |

OTHER PUBLICATIONS

Allshire et al., "A fission yeast chromosome can replicate autonomously in mouse cells," *Cell* Jul. 31;50(3):391–403 (1987).
Brenneman et al., "Stimulation of intrachromosomal homologous recombination in human cells by electroporation with site-specific endonucleases," *Proc. Natl. Acad. Sci. USA* 93:3608–3612 (1996).
Broach et al., "Transformation in yeast: development of a hybrid cloning vector and isolation of the CAN1 gene," *Gene* 8(1):121–33 (1979).
Broach et al., "Circular DNA plasmids of yeasts," *In The Molecular and Cellular Biology of the Yeast Saccharomyces*, vol. 1 (E.W. Jones, J.R. Pringle, and J.R. Broach, eds.) Cold Spring Harbor Laboratory Press, pp. 297–331 (1991).
Burke et al., "Cloning of large segments of exogenous DNA into yeast by means of artificial chromosome vectors." *Science* 15;236(4803):806–12 (May 1987).

Cavalier–Smith T. "The simultaneous symbiotic origin of mitochondria, chloroplasts, and microbodies," *Ann N Y Acad Sci* 503:55–71 (1987).
Cossart P. "Interactions of the bacterial pathogen Listeria monocytogenes with mammalian cells: bacterial factors, cellular ligands, and signaling," *Folia Microbiol (Praha)* 43(3):291–303 (1998).
Curran et al., "Protoplast fusion in *Saccharomyces cerevisiae*," In Methods in Molecular Biology, Yeast Protocols, vol. 53 (I. Evans, ed.), Humana Press, Inc., Totowa, NJ, pp. 45–49 (1996).
Demoss "Biochemical Diversity in the Tryptophan Pathway," *Biophys. Res. Comm.* 18:850 (1964).
Douglas "Chloropast Origins and Evolution," *In Molecular Biology of Cyanobacteria*, vol. 1 (Bryant, ed.) Kluwer Academic Publishers, Boston, pp. 91–118 (1994).
Elhai et al., "Conjugal transfer of DNA to cyanobacteria," *Methods Enzymol* 167:747–54 (1988).
Fasiolo et al., "Cloning of the yeast methionyl–tRNA synthetase gene," *J Biol Chem* 10;256(5):2324–8 (Mar. 1991).
Fox et al., "Analysis and manipulation of yeast mitochondrial genes," *Methods of Enzymol.* 194: 149–165 (1991).
Fox et al., "Plasmids can stably transform yeast mitochondria lacking endogenous mtDNA," *Proc Natl Acad Sci U S A.* 85(19):7288–92 (Oct. 1988).
Gimble et al., "Purification and characterization of VDE, a site-specific endonuclease from the yeast *Saccharomyces cerevisiae*," *J Biol Chem.* 15;268(29):21844–53 (Oct. 1993).
Grimes et al., "Engineering mammalian chromosomes," *Hum Mol Genet.*7(10):1635–40 (1998).
Grivell LA. "Nucleo–mitochondrial interactions in mitochondrial gene expression," *Crit Rev Biochem Mol Biol.* 30(2):121–64 (1995).
Hanahan D. "Studies on transformation of *Escherichia coli* with plasmids," *J Mol Biol.* 5;166(4):557–80 ( Jun. 1983).
Harrington et al., "Formation of de novo centromeres and construction of first–generation human artificial microchromosomes," *Nat Genet.* 15(4):345–55 (Apr. 1997).
Herskowitz et al., "Mating–type determination and mating–type inter conversion in *Saccharomyces cerevisiae*," In The Molecular and Cellular Biology of the Yeast Saccharomyces, vol. 2 (E.W. Jones, J.R. Pringle, and J.R. Broach, eds.) Cold Spring Harbor Laboratory Press, pp. 583–656 (1992).
Herskowitz et al., "Putting the HO gene to work: practical uses for mating–type switching," *Methods Enzymol.* 194:132–46 (1991).

(List continued on next page.)

*Primary Examiner*—Terry McKelvey
(74) *Attorney, Agent, or Firm*—Richard F. Trecartin; Dorsey & Whitney, LLP

(57) ABSTRACT

The present invention is directed to novel recombinant nucleic acids for introducing yeast chromosomal elements into the genomes of bacteria. The invention provides methods to convert the modified bacterial genomes into artificial yeast chromosomes by fusing the bacteria with yeast that linearize the modified bacterial genomes, to produce artificial chromosomes.

23 Claims, 7 Drawing Sheets

OTHER PUBLICATIONS

Huang et al., "Convenient and Reversible Site–Specific Targeting of Exogenous DNA into a Vacterial Chromosome by Use of the FLP Recombinase: the FLIRT System," *J. of Bacteriology*, 179(19): 6076–6083 (1997).

Kelleher et al., "A novel activity in *Escherichia coli* K–12 that directs restriction of DNA modified at CG dinucleotides," *J Bacteriol.* 173(16):5220–3 (Aug. 1991)..

Kingston et al., "Electroporation into Plant Protoplasts," *In Current Protocols in Molecular Biology*, vol. 1 (F. Ausubel, R. Brent, R. Kingston, D. Moore, J. Seidman, J. Smith, and K. Struhl, eds.) John Wiley & Sons, pp. 9.3.2–9.3.3 (1997).

Kladde et al., "Chromatin structure mapping in vivo using methyltransferases," *Methods Enzymol.* 274:214–33 (1996).

Kostriken et al., "The product of the HO gene is a nuclease: Purification and Characterization of the enzyme," *Cold Spring Harbor Symp. Quant. Biol.* 49:89–96 (1984).

Larin et al., "Generation of Large Insert YAC Libraties," *Methods in Molecular Biology*, YAC protocols, vol. 54 (D. Markie, ed), Human Press Inc., Totowa, NJ, pp. 1–11 (1996).

Lundblad, V. "*Saccharomyces cerevisiae*," *In Short Protocols in Molecular Biology* Third Edition (F. Ausubel, R. Brent, R. Kingston, D. Moore, J. Seidman, J. Smith, and K. Struhl, eds.) John Wiley & Sons, pp. 13–1 thru 13–29 (1995).

Marsh et al., "The pathway of cell and nuclear fusion during mating in *S. cerevisiae*," *In The Molecular and Cellular Biology of the Yeast Saccharomyces*, vol. 3 (E.W. Jones, J.R. Pringle, and J.R. Broach, eds.) Cold Spring Harbor Laboratory Press, pp. 827–888 (1997).

Mollenhauer "Geosiphon pyriforme," *In Algae and Symbiosis*. Biopress Ltd., Bistol, pp. 339–351 (1992).

Murray et al., "Construction of artificial chromosomes in yeast," *Nature* 15–21;305(5931):189–93 (Sep. 1983).

Nickoloff "In vivo analysis of the *Saccharomyces cerevisiae* HO nuclease recognition site by site–directed mutagenesis," *Mol Cell Biol.* 10(3):1174–9 (Mar. 1990).

Pizarro–Cerda et al., "When intracellular pathogens invade the frontiers of cell biology and immunology," *Histol Histopathol.* 12(4):1027–38 (Oct. 1997).

Pon et al., "Biogenesis of mitochondria," *In The Molecular and Cellular Biology of the Yeast Saccharomyces*, vol. 1 (E.W. Jones, J.R. Pringle, and J.R. Broach, eds.) Cold Spring Harbor Laboratory Press, pp. 333–406 (1991).

Prince et al., "Gene transfer: a review of methods and applications," *Pathology* 30(4):335–47 (Nov. 1998).

Rassoulzadegan et al., "High frequency of gene transfer after fusion between bacteria and eukaryotic cells." *Nature* 295(5846):257–9 (Jan. 21, 1982).

Rhodes et al., "Genetically transformed maize plants from protoplasts," *Science* 8;240(4849):204–7 (Apr. 1988).

Round et al., "*Arabidopsis thaliana* Centromere Regions: Genetic Map Positions and Repetitive DNA Structure," *Genome Research*, 7:1045–1053 (1997).

Sambrook et al., "Introduction of recombinant vectors into mammalian cells," *In Molecular Cloning, A Laboratory Manual*, 2nd edition vol. 3 (C. Nolan, ed.), Cold Spring Harbor Laboratory Press, Cold Spring Harbor, NY, pp. 16.30–16.81 (1989).

Sargent et al., "Repair of Site–Specific Double–Strand Breaks in a Mammalian Chromosome by Homologous and Illegitimate Recombination," *Molecualr and Cellular Biology* 17(1): 267–277 (1997).

Sikorski et al., "A system of shuttle vectors and yeast host strains designed for efficient manipulation of DNA in *Saccharomyces cerevisiae*," *Genetics* 122(1):19–27 (May 1989).

Stinchcomb et al., "Isolation and characterisation of a yeast chromosomal replicator," *Nature* 1;282(5734):39–43 (Nov. 1979).

Valentin et al. "Phylogenetic origin of the plastids," *In Origins of Plastids* (Lewin, ed.) Chapman and Hall, New York, pp. 193–221 (1992).

Woodcock et al., "Quantitative evaluation of *Escherichia coli* host strains for tolerance to cytosine methylation in plasmid and phage recombinants," *Nucleic Acids Res.* 17(9):3469–78 (May 11, 1989).

Zhang et al., "Metabolic engineering of a pentose metabolism pathway in ethanologenic *Zymomonas mobilis*" *Science* 267:240–243 (1995).

* cited by examiner

A= pYAC

B= pAYAC

Fig. 7
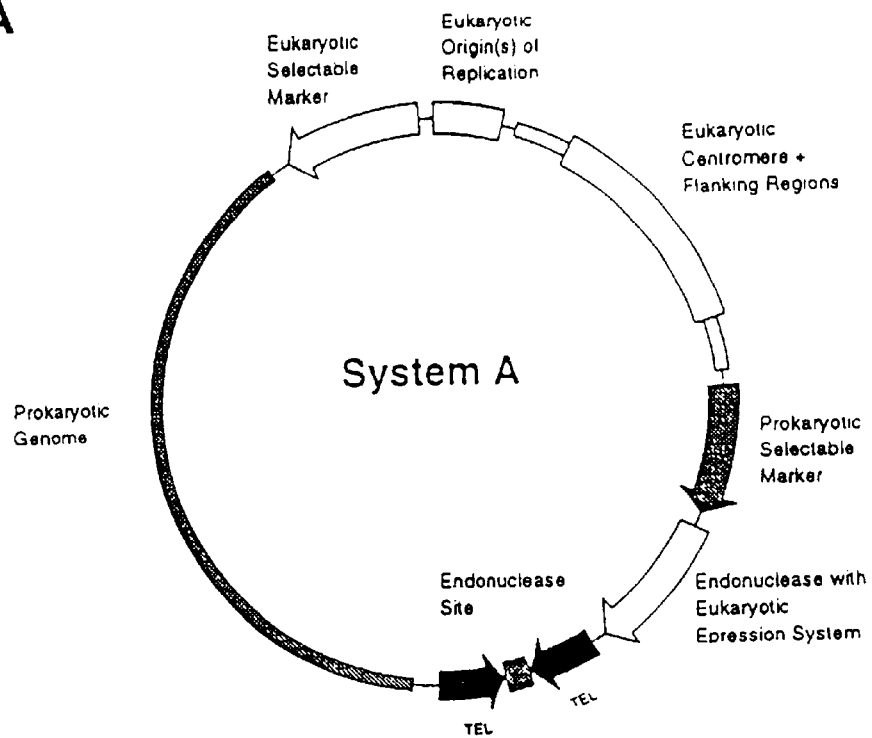
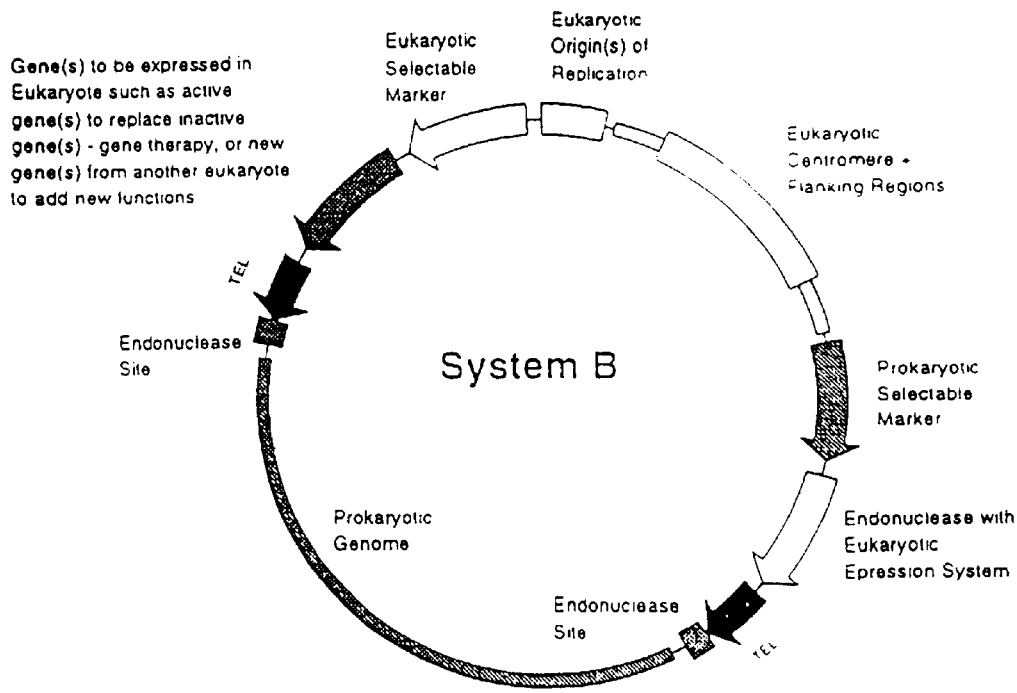

```
                            SEQUENCE LISTING

<160> NUMBER OF SEQ ID NOS: 10

<210> SEQ ID NO 1
<211> LENGTH: 102
<212> TYPE: DNA
<213> ORGANISM: Saccharomyces cerevisiae
<220> FEATURE:
<221> NAME/KEY:
<222> LOCATION:
<300> PUBLICATION INFORMATION:
<301> AUTHORS:
<302> TITLE:
<303> JOURNAL:
<304> VOLUME:
<305> ISSUE:
<306> PAGES:
<307> DATE:

<400> SEQUENCE: 1
aattcagatc tgggactact tcgcgcaaca gtaaaatttt ataaacccgg ggatccttta      60
taaaatttta ctgttgcgga aagctgaaac taatctagat ct                       102

<210> SEQ ID NO 2
<211> LENGTH: 102
<212> TYPE: DNA
<213> ORGANISM: Saccharomyces cerevisiae

<400> SEQUENCE: 2
agctagatct agattagttt cagctttccg caacagtaaa attttataaa ggatccccgg      60
gtttataaaa ttttactgtt gcgcgaagta gtcccagatc tg                       102

<210> SEQ ID NO 3
<211> LENGTH: 102
<212> TYPE: DNA
<213> ORGANISM: Saccharomyces cerevisiae

<400> SEQUENCE: 3
aattcggatc catctatgtc gggtgcggag aaagaggtaa tgaaatggca agatcttgcc      60
atttcattac ctctttctcc gcaccgaca tagatggatc cg                        102

<210> SEQ ID NO 4
<211> LENGTH: 102
<212> TYPE: DNA
<213> ORGANISM: Saccharomyces cerevisiae

<400> SEQUENCE: 4
aattcggatc catctatgtc gggtgcggag aaagaggtaa tgaaatggca agatcttgcc      60
atttcattac ctctttctcc gcaccgaca tagatggatc cg                        102

<210> SEQ ID NO 5
<211> LENGTH: 51
<212> TYPE: DNA
<213> ORGANISM: Saccharomyces cerevisiae

<400> SEQUENCE: 5
aattcagatc tgggactact tcgcgcaaca gtaaaatttt ataaacccgg g              51
```

-continued

```
<210> SEQ ID NO 6
<211> LENGTH: 51
<212> TYPE: DNA
<213> ORGANISM: Saccharomyces cerevisiae

<400> SEQUENCE: 6
gatccccggg tttataaaat tttactgttg cgcgaagtag tcccagatct g          51

<210> SEQ ID NO 7
<211> LENGTH: 51
<212> TYPE: DNA
<213> ORGANISM: Saccharomyces cerevisiae

<400> SEQUENCE: 7
gatcctttat aaaattttac tgttgcggaa agctgaaact aatctagatc t          51

<210> SEQ ID NO 8
<211> LENGTH: 51
<212> TYPE: DNA
<213> ORGANISM: Saccharomyces cerevisiae

<400> SEQUENCE: 8
agctagatct agattagttt cagctttccg caacagtaaa attttataaa g          51

<210> SEQ ID NO 9
<211> LENGTH: 51
<212> TYPE: DNA
<213> ORGANISM: Saccharomyces cerevisiae

<400> SEQUENCE: 9
aattcggatc catctatgtc gggtgcggag aaagaggtaa tgaaatggca a          51

<210> SEQ ID NO 10
<211> LENGTH: 51
<212> TYPE: DNA
<213> ORGANISM: Saccharomyces cerevisiae

<400> SEQUENCE: 10
gatcttgcca tttcattacc tctttctccg cacccgacat agatggatcc g          51
```

AUTOMATIC EUKARYOTIC ARTIFICIAL CHROMOSOME VECTOR

The subject application was filed as application Ser. No. PCT/US99/16297 on Jul. 26, 1999, which claims the benefit of the filing date of application U.S. Ser. No. 60/094,294, filed Jul. 27, 1998, closed.

FIELD OF THE INVENTION

The present invention relates to novel recombinant nucleic acids and methods for their use to introduce a prokaryotic genome or other valuable DNA into a eukaryotic cell as a circular molecule that is then converted to a linear automatic eukaryotic artificial chromosome within the eukaryotic nucleus and as a circular chromosome within a membrane bound, extranuclear element. Such added prokaryotic genomes or other valuable DNAs should add new functions to the eukaryotes or allow them to be selected for using this hybrid system.

BACKGROUND OF THE INVENTION

Evolutionary theory proposes that mitochondria and plastids originated by engulfment or cell fusion of prokaryotes by eukaryotes. As this relationship evolved, the size of the bacterial DNA genome decreased and the functions of genes lost from the bacterial genome were assumed by the eukaryotic chromosome (Cavalier-Smith. (1987) *Ann. NY Acad. Sci.* 503:55–71). Support for this theory is found in the fungus, *Geosiphon pyriforme*, which contains in its hyphal system cyanobacteria belonging to the genus, Nostoc, but which retain the capacity for autonomous growth and replication (Mollenhauer. (1992) *Geosiphon pyriforme, In Algae and Symbiosis*. Biopress Ltd., Bistol, pp. 339–351). Additional support is found in algae which have plastids containing DNA that has a significant level of homology and similar gene organization to cyanobacteria but the plastids have lost most of the cyanobacterial genes to the cell nucleus (Douglas. (1994) Chloropast Origins and Evolution, In *Molecular Biology of Cyanobacteria*, vol. 1 (Bryant, ed.) Kluwer Academic Publishers, Boston, pp. 91–118). The reason and mechanism for the relocation of a large proportion (greater than 90%) of the bacterial genes to the nucleus are unknown (Valentin et al. (1992) Phylogenetic origin of the plastids, In *Origins of Plastids* (Lewin, ed.) Chapman and Hall, New York, pp. 193–221).

It would therefore be useful to develop a system to introduce an entire prokaryotic genome into a eukaryotic organism and to study the interactions of the two genomes and the effect this has on both organisms. Preferably, such a system would permit both nuclear and extra-nuclear localization of the bacterial genome. This system also would provide a model for the evolution of mitochondria, chloroplasts, and other plastids.

The present invention presents new technology that can be used to transfer entire bacterial chromosomes into yeast or other eukaryotic organisms in such a manner that they become functional linear artificial chromosomes and, furthermore, may become compartmentalized bacteria or organelle-like structures. The bacterial chromosome will be expressed partially in the nucleus and in the bacterial organelle and provides new and useful pathways to the eukaryote host immediately after formation of the hybrid cell or after selections for specific desired functions norm ally done by the prokaryote alone as well as new functions. These new vectors and methods additionally provide a means to efficiently introduce very large segments of DNA into eukaryotic cells without extracellular manipulation.

SUMMARY OF THE INVENTION

The present invention provides compositions and methods for transferring an entire prokaryotic genome or other DNAs into a eukaryotic organism. In one aspect, the invention provides a recombinant expression system to introduce an endonuclease gene with a rare cleavage site into a eukaryotic organism as well as using endonuclease(s) already present in the eukaryote. In another aspect, the invention provides circular recombinant nucleic acids that are converted by the endonuclease to automatic, eukaryotic artificial chromosomes. The invention also provides a recombinant nucleic acid for converting a prokaryotic genome into a eukaryotic chromosome. In yet another aspect, the invention provides methods for introducing converted bacterial genomes and circular DNAs into a eukaryotic organism. Finally, the invention also provides methods for selecting eukaryotic organisms comprising the modified bacterial chromosome or other DNAs, as well as the selectable addition of new valuable functions from the prokaryotes or other DNAs being added to the eukaryotic cell.

BRIEF DESCRIPTION OF THE DRAWINGS

FIGS. 7A–7B show the general structure of elements for genomes to be used as pAEAC's. The general structure of a pAEAC for use in transfer of prokaryotic genomes into eukaryotic cells is shown in Panel A. Panel B shows the general structure of a pAEAC to be used for gene therapy or the addition of specific gene systems into eukaryotic cells without the incorporation of the prokaryotic genome sequences. The functional elements are identified but are not drawn to scale.

DETAILED DESCRIPTION OF THE PREFERRED EMBODIMENTS

1. Definitions

Figure 1:
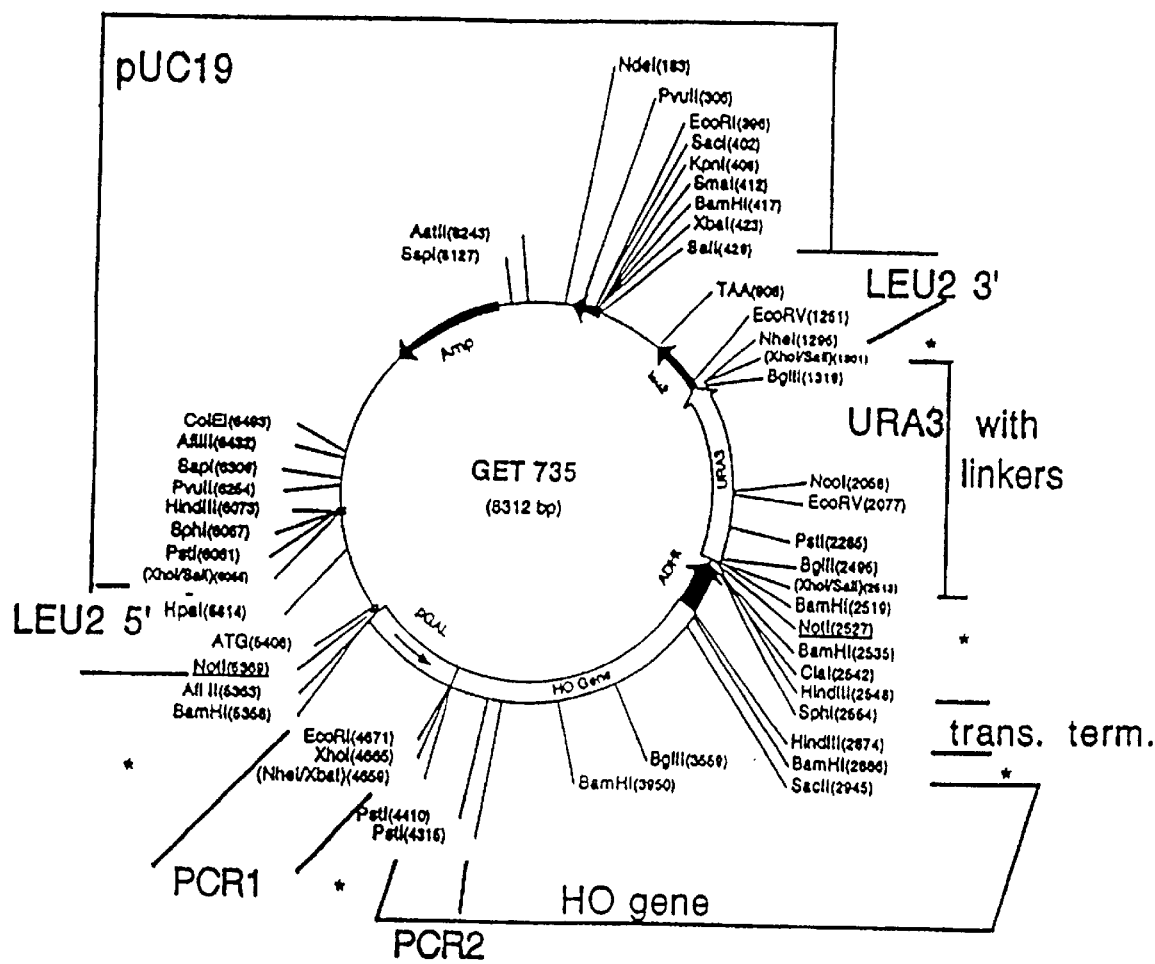
FIG. 1 shows plasmid GET1735 and the origin of the components used for its construction: Yeast LEU2 5' region, pUC19, LEU2 3' region, URA3 promoter and terminator, and the HO restriction enzyme gene operatively linked to the pGAL10 promoter and alcohol dehydrogenase (ADHt) 3' transcription terminator.

The term "automatic yeast artificial chromosome" (AYAC) when used herein encompasses a circular recombinant nucleic acid molecule that is converted to a linear yeast chromosome in vivo by an endogenously expressed restriction endonuclease. For use in other eukaryotic species this is called an "automatic eukaryotic artificial chromosome" or AEAC. The recombinant nucleic acid carries appropriately oriented sequences that function as telomeres in the eukaryote and sequences that function as centromeres in the eukaryote used, and a replication origin(s) for autonomous replication within yeast or other eukaryotes. The recombinant nucleic acid should contain selectable markers that work both in the prokaryotes and the eukaryotes.

A "recombinant" or "isolated" nucleic acid molecule comprising the various nucleic acid sequences disclosed herein, means a nucleic acid molecule that has been assembled by molecular biological techniques to contain sequences of defined function that are operably linked.

The term "control sequences" refers to DNA sequences necessary for the expression of an operably linked coding sequence in a particular host organism. The control sequences that are suitable for prokaryotes, for example, include a promoter, optionally an operator sequence, and a ribosome binding site. Eukaryotic cells are known to utilize promoters, polyadenylation signals, and enhancers.

A nucleic acid is "operably linked" when it is placed into a functional relationship with another nucleic acid sequence. For example, DNA for a presequence or secretory leader is operably linked to DNA for a polypeptide if it is expressed as a preprotein that participates in the secretion of the polypeptide; a promoter or enhancer is operably linked to a coding sequence if it affects the transcription of the sequence; a ribosome binding site is operably linked to a coding sequence if it is positioned so as to facilitate translation. Generally, "operably linked" means that the DNA sequences being linked are contiguous, and, in the case of a secretory leader, contiguous and in reading phase. However, enhancers do not have to be contiguous. Linking is accomplished by ligation at convenient restriction sites. If such sites do not exist, the synthetic oligonucleotide adaptors or linkers are used in accordance with conventional practice.

II. Compositions and Methods of the Invention

The present invention provides recombinant nucleic acids and methods for their use for the transfer of an entire prokaryotic genome or other useful DNAs into a eukaryotic organism. This transfer may be used to study the origins of prokaryotic-like organelles, such as mitochondria and chloroplasts, or to add new functions and pathways to a eukaryotic organism such as, but not limited to, photosynthesis, nitrogen fixation, thermal or salt resistance, motility, mixed antibiotic pathways, non-mutated eukaryotic genes (e.g. gene therapy), etc.

The present invention provides a recombinant nucleic acid that functions as an automatic yeast artificial chromosome (AYAC) or more generally an automatic eukaryotic artificial chromosome (AEAC). pAYACs are circular plasmids composed of a yeast selectable marker, an ARS sequence (or foreign sequences which have ARS-like functions) for replication in yeast, a centromere that is functional in yeast, at least two inverted Tetrahymena or yeast telomeres (or telomeres from other species that function in yeast), one or more rare restriction endonuclease sites between the two inverted telomeres, a prokaryotic selectable marker, and flanking prokaryotic sequences for integration into a bacterial chromosome by homologous recombination. pAYACs also preferably contain a second prokaryotic selectable marker and a prokaryotic replication origin that can be removed prior to integration into the circular DNA of the prokaryotes. Some contain the chosen endonuclease gene expressed using the appropriate eukaryotic transcription/translation DNA signals.

The pAYAC vectors are linearized by restriction enzyme digestion and transformed into a prokaryotic organism where they integrate into a circular prokaryotic chromosome by homologous recombination or by the use of other integration methods. Successfully transformed and recombined prokaryotes are preferably isolated by a selectable marker encoded by the integrated pAYAC vector and, subsequently, undergo protoplast fusion to a yeast strain that produces a specific endonuclease, located in the nucleus, that cuts the integrated pAYAC between the inverted telomeres at the endonuclease(s) sites. Once linearized in the nucleus of a eukaryotic host, the bacterial genome functions as an artificial yeast chromosome. Selectable markers such as drug resistance genes or genes that complement yeast auxotrophies ensure the presence and maintenance of the artificial chromosome. If the bacterial chromosome is too large for maintenance in the yeast as a single molecule, additional pAYAC vectors may be inserted into the circular bacterial genome at various locations to allow the genome to be broken down into smaller yeast chromosomes. The establishment of a fused bacterium as an organelle following protoplast fusion may also occur. However, the establishment of the bacterium as an organelle preferably requires a second protoplast fusion with an identical bacterium that does not contain an integrated pAYAC using a different selectable marker. In either instance, selection for new bacterial enzymes or pathways can then be used to isolate the yeast or eukaryote with desired newly acquired characteristics.

One advantage of this system over existing technologies is that an entire genome from one organism can be easily introduced into a second organism without in vitro manipulation. This is accomplished by first modifying a prokaryotic (e.g. bacterial) genome in vivo and introducing the entire genome into a eukaryotic organism, such as, but not limited to, a yeast, by protoplast fusion of both the bacterium and the eukaryote. New functions are then selected for, such as mitochondrial function in rho$^-$ or rho$^\circ$ yeast (little or no unique mitochondrial DNA and loss of mitochrondrial function), photosynthesis (growth with $CO_2$, $H_2O$, light, salts, and minerals), nitrogen fixation (growth using atmospheric $N_2$ as, the sole nitrogen source), growth at high temperatures following thermophilic bacterial fusions, motility, creation of new antibiotics from the combination of bacterial antibiotic pathways from more than one bacterial strain, complementation of a mammalian genetic defect (i.e. gene therapy), etc.

A second advantage of this method is that large DNA segments are easily manipulated and introduced into yeast or other eukaryotes. The length of YACs made by conventional methods are somewhat limited and average about 1 Mbp (Larin, Z., Monaco, A. P., and Lehrach, H. (1996) Generation of large insert YAC libraries, In *Methods in Molecular Biology*, YAC Protocols, vol. 54 (D. Markie, ed.), Humana Press Inc., Totowa, N.J., pp. 1–11). This size constraint results from a required in vitro ligation of the DNA insert to the YAC vector ends prior to yeast transformation. Although the technology has improved over the years, much larger pieces (3.5 Mbp) have only been transferred by protoplast fusions (Allshire et al. (1987) *Cell* 50:391–403). In the examples provided below, the entire *E. coli* genome (4.7 Mbp) will be introduced into a yeast as a circle which is then automatically (via the rare endonuclease activity in the nucleus) converted to a linear automatic yeast artificial chromosome.

The fused eukaryotic organism is, for example, a fungi, a yeast, a protozoa, a plant, an animal cell, a human cell, or a eukaryotic microrganism. Eukaryotic cell or cell lines, such as, vertebrate, invertebrate or plant cells also can be used. The eukaryotic organism preferably expresses an endonuclease that cleaves at a rare site located between the inverted telomeres of the AYAC or AEAC, thereby, converting it into a linear artificial chromosome. Alternatively, the specific endonuclease can be expressed by the AEAC or AYAC vector sequences, from a genomic element integrated into the host genome, or from an extrachromosomal element such as a plasmid or virus vector (can also be an integrated virus). In either case, the restriction endonuclease is operably linked to eukaryotic control sequences, such as a eukaryotic promoter and transcription termination elements.

The prokaryotic organism is, for example, a eubacterium, a cyanobacterium, an archaebacterium. It may have a specific phenotype; for example, a nitrogen-fixing bacterium, a thermophilic bacterium or a prokaryote that produces antibiotics. Examples of prokaryotes include but are not limited to *Escherichia coli, Zymomonas mobilis*, Azotobacter, Rhizobium, Streptomyces, Synechococcus PCC6301, and Anabaena PCC7120.

Selecting the correct endonuclease recognition site is important to AEAC function. Preferably, specific endonucleases are utilized that are characterized by having long restriction site recognition sequences that occur infrequently, hence, rare. Examples of these endonuclease recognition sites include, but are not limited to, HO (24 bp), I-ScelI (18 bp), and PI-ScelI (31 bp). Before choosing a particular endonuclease recognition site, the endonuclease should be expressed in the bacterium and in the eukaryote organism or cell to ensure that the genomes of these organisms are not digested by the chosen enzyme in a way that is toxic to the organism. For example, at least one HO endonuclease site it thought to be present in *E. coli* genomic DNA since production of the yeast HO endonuclease is toxic to recA⁻ *E. coli* cells, recA⁺ cells, however, are not affected, probably due to repair of occasional double strand breaks by the recA gene product (Kostriken, R. and Heffron, F. (1984) The product of the HO gene is a nuclease: Purification and Characterization of the Enzyme, *Cold Spring Harbor Symp.* *Quant. Biol.* 49:89–96). However, it should be noted that HO endonuclease is also reported to cleave non-MAT yeast DNA in vitro even though only the HO site in MAT is cleaved in vivo. Comparison of possible HO endonuclease target sequences in vitro and in vivo indicates that the HO endonuclease has a lower specificity in vitro (Nickoloff, J. A., et al., (1990) In Vivo Analysis of the *Saccharomyces cerevisiae* HO Nuclease Recognition Site by Site-Directed Mutagenesis, *Mol. Cell. Biol.* 10:1174–1179). These observations might account for the apparent cleavage of *E. coli* genomic DNA. It is also highly likely that in the yeast nucleus (in vivo) the HO endonuclease will only cleave the pAYAC plasmid containing the *E. coli* genome at the desired HO endonuclease sites next to the telomeres. I-Scel endonuclease sites are not present in a mammalian genome (CHO cells, Chinese hamster ovary); however, engineered sites introduced into the genome are cut by added endonuclease and lead to toxicity and death accompanied by high recombination frequencies (Sargent, R. G., Brenneman, M. A., and Wilson, J. H. (1997) Repair of site-specific double-strand breaks in a mammalian chromosome by homologous and illegitimate recombination, *Mol. and Cell. Biol.* 17: 267–277). PI-Scel endonuclease sites are most likely not present in the human genome since PI-SceI endonuclease placed in human cells has little or no effect on viability (Brenneman, M., Gimble, F. S., and Wilson, J. H. (1996) Stimulation of intrachromosomal homologous recombination in human cells by electroporation with site-specific endonucleases, *Proc. Natl. Acad. Sci. USA* 93: 3608–3612).

Any chromosome that is circular and is not susceptible to the chosen endonuclease in its genome may be transferred into the yeast or other eukaryotic organisms (e.g. plants, fungi, or animals). Preferably, the yeast or eukaryotic host must also be resistant to the chosen endonuclease. The endonuclease site should not be present in the eukaryotic genome; except for example, HO endonuclease recognition site present in the MAT locus found on yeast chromosome III (Herskowitz, I., Rhine, J., and Strathern, J. (1992) Mating-type determination and mating-type inter conversion in Saccharomyces cerevisiae, In *The Molecular and Cellular Biology of the Yeast Saccharomyces*, vol. 2 (E. W. Jones, J. R. Pringle, and J. R. Broach, eds.) Cold Spring Harbor Laboratory Press, pp. 583–656). Cutting at this site precedes mating type conversion and is not lethal to the cell. Moreover, in the examples that follow, the HO endonuclease was successfully expressed in yeast and used to convert pAYAC vectors into linear chromosomes with mating type switching being a control for active HO endonuclease function.

Figure 6:
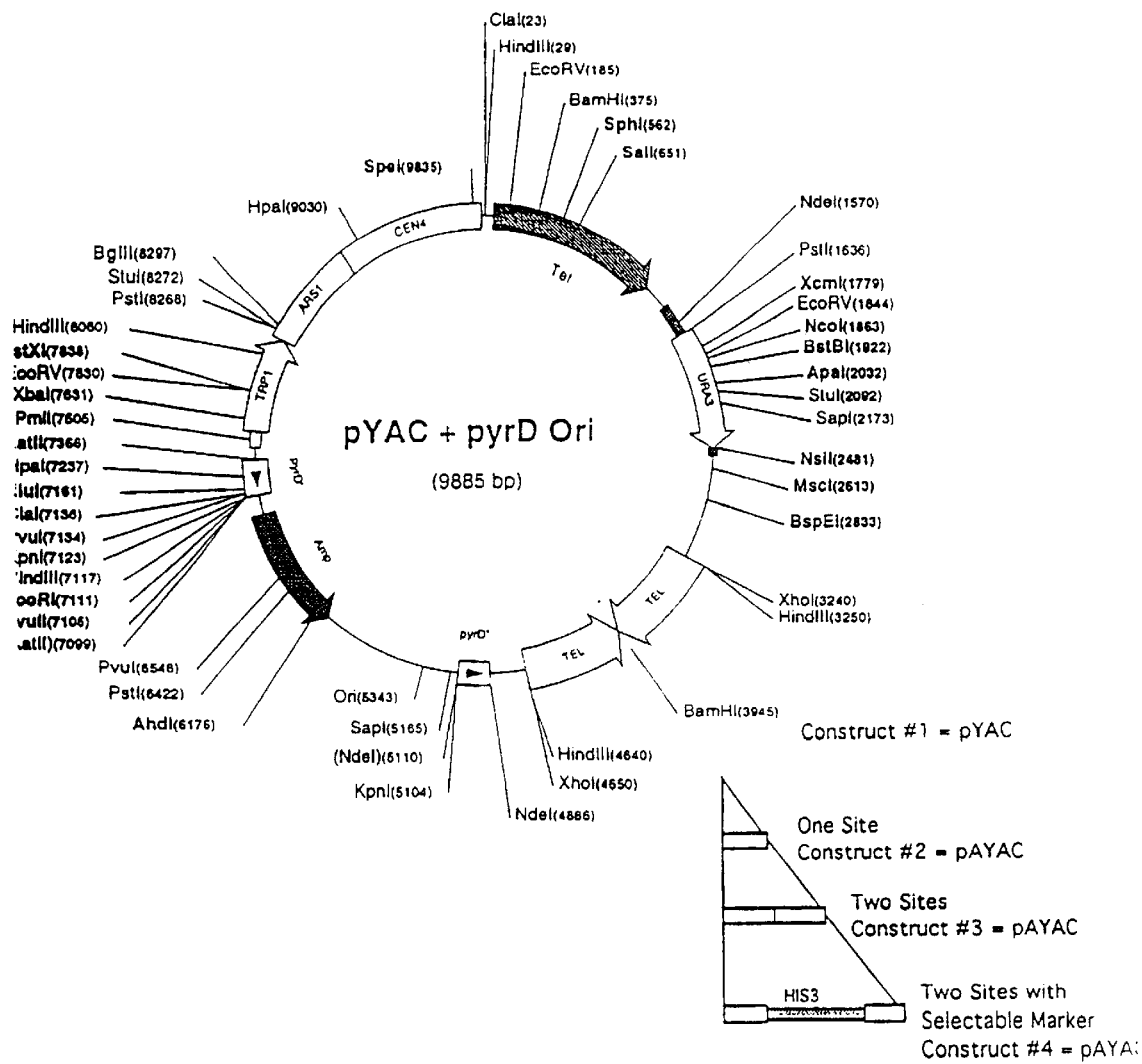
FIG. 6 shows pYAC+pyrD Ori plasmid. The *E. coli* pyrD sequences are shown as boxed regions with an arrow in them showing the direction of transcription in this gene. Other functional units are boxed. The origin of replication which works in *E. coli* is designated. pAYAC plasmids are all constructs other than #1. The "Site" referred to in Constructs #2–#4 is any desired endonuclease cleavage site (e.g. MATα HO, MATα HO, PI-SceI or any other enzyme site) while the selectable marker is any yeast selectable marker (HIS3 is used as an example only).

In the pAYAC vectors, the specific rare restriction site is placed directly between the inverted telomeres (see FIGS. 6 & 7 for alternative conformations). The pAYAC vectors also contain all elements required of a yeast chromosome such as a functional centromere and at least one functional yeast origin of replication. Preferably, at least one eukaryotic and one prokaryotic selectable marker is included. The pAYAC vector also contains DNA from a specific gene of a desired bacterium which is disrupted by the insertion of an origin of replication functional in *E. Coli* or other convenient vector and, preferably, a second prokaryotic selectable marker. The bacterial replication origin is, for example, the pBR322 origin, and the prokaryotic selectable marker is, for example, the ApR (ampicillin resistance). These sequences are present only for convenience to manipulate the pAYAC vector as a bacterial plasmid and are removed prior to integration into the bacterial genome. In addition, the absence of the ApR gene is preferred for protoplasting the bacterium and for making stable bacterial mitochondria due to the inhibition of peptidoglycan crosslinking or cell wall formation.

Transformation of the bacterium is performed after the bacterial origin and ApR gene (optional) are removed from the plasmid by restriction digestion. The bacterial origin must be removed only if the *E. coli* replication origin from pBR322 works in the target bacterium. The linearized DNA is integrated into the circular genome of the bacterium by recombination between the disrupted bacterial DNA sequence on the linearized pAYAC and the homologous sequence in the bacterial genome. After selecting for various antibiotic resistances or other markers on the DNA fragment, bacteria containing a recombinant genome are isolated. The phenotype of the disrupted gene in the transformed bacterium verifies integration of the plasmid at the correct site.

The transformed bacterium is then spheroplasted using lysozyme or ampicillin and fused with a yeast protoplast, produced using an enzyme such as a glucanase (e.g. glusulase and zymolyase). The yeast protoplast contains multiple mutations (or, alternatively, no mutations if antibiotic resistance is selected for in yeast using a yeast driven promoter) and expresses an active endonuclease under the control of a yeast constitutive or inducible promoter from a plasmid or integrated DNA. After protoplast fusion the entry of the circular bacterial DNA into the yeast nucleus is selected for using various yeast markers (i.e., TRP1 and URA3) present in the pAYAC integrated into the bacterial genome. The endonuclease cleaves the recombinant bacterial genome, resulting in the formation of a functional automatic yeast artificial chromosome, The placement of the entire bacterial chromosome into a yeast nucleus as an artificial chromosome or in the cytoplasm as a bacterial organelle will provide all the information required for bacterial functions. For example, because *E. coli* can grow on xylose as a carbon source and yeast cannot (but do transport it), selection for yeast that utilize xylose as a carbon source can be conveniently used as a marker for expression and functioning of the bacterial genome. Fusion of bacteria containing the AYAC vector with a rho⁻ or rho° (mitochondrial function and DNA deficient) yeast will be examined for growth on glycerol/ethanol media which requires complex complementation of many pathways or genes in yeast. The rho° complementation will require the bacterial replacement of at least 19–23 genes as well as 27 RNA transcriptional units of the yeast mitochondrial DNA (varies in size from 74–85 kbp) and the possible function of an estimated 215 genes located in the nucleus. (Grivell, L. A. (1995) Nucleo-mitochondrial interactions in mitochondrial gene expression, *Critical Rev. in Biochem. and Mol. Biol.* 30: 121–16). These pathways as well as other individual mutations may be complemented by similar functions supplied by the correct functioning of the bacterial DNA as a yeast chromosome or as a circular chromosome in a membrane bound organelle.

The establishment of a bacterial organelle preferably requires the presence of ampicillin or mutations in the bacterium preventing peptidoglycan cross-linking or synthesis in order to prevent the formation of a cell wall. The transformation and complementation of rho⁻ or rho° yeast with in vitro isolated wild-type or mutant mitochondria (Pon L., and Schatz, G. (1991) Biogenesis of mitochondria, in *The Molecular and Cellular Biology of the Yeast Saccharomyces*, vol. 1 (E. W. Jones, J. R. Pringle, and J. R. Broach, eds.) Cold Spring Harbor Laboratory Press, pp. 333–406) indicates that the bacterial cell may also form a functional organelle. In addition to protoplast fusion to make the desired organism, whole mitochondrial transformation by use of metal projectiles that are shot into yeast cells by a particle gun indicates that such bacteria may be injected into plants, tissues, and cells using this method (T. D. Fox et al. (1988) *Proc. Natl. Acad. Sci. USA* 85:7288–7292).

Once the eukaryote-prokaryote hybrids are made, new functions of the eukaryote are noted, characterized, or selected for. Additional evidence of bacterial gene expression is determined using specific inhibitors of prokaryotes that do not affect eukaryotes, such as rifampicin (inhibits RNA synthesis in some bacteria), chloramphenicol (inhibits peptidyl transferase in translation), erythromycin (inhibits translocation in translation), fusidic acid (inhibits elongation in translation), streptomycin (inhibits chain initiation in translation), and tetracycline (inhibits binding of aminoacyl-tRNAs to ribosome).

Technical limitations associated with these hybrid bacterial/eukaryotic systems can be anticipated. For example, restriction modification systems in various bacteria may degrade the yeast or eukaryotic DNA. Therefore, *E. coli* strains that are deficient in restriction and modification systems are preferable. This is evidenced by protoplast fusions of bacterial and human cells Rassoulzadegan, M., Binetruy, B. and Cusin, F. (1982) High frequency of gene transfer after fusion between bacteria and eukaryotic cells, *Nature* 295:257). Although yeast DNA is not methylated, methylation by several heterologous bacterial enzymes (dam, the Sau3AI, and the SssI methyltransferases) does not appear to effect viability or inhibit cellular functions (Kladde, M. P., and Simpson, R. T. (1996) Chromosome structure mapping in vivo using methyltransferases, *Methods in Enzymol.* 274:214–233). This indicates that pretreatment of the yeast (and other eukaryotes) with the appropriate methyltransferases preferably makes their chromosomal DNAs resistant to specific restriction enzymes from a bacterium that is restriction competent. This procedure has been successfully employed for cloning of DNA from a bacterium into a cyanobacterium (Elhai, J., and Wolk, C. P. (1988) Conjugal transfer of DNA to cyanobacteria, *Methods in Enzymol.* 167:747–754). Proteases also may be problematic when the bacterial cell lyses during fusion and releases its contents; however, this was not a problem when fusing *E. coli* to human cells, described above (Sambrook, J., Fritsch, E. F., and Maniatis, T. (1989) Introduction of recombinant vectors into mammalian cells. In *Molecular Cloning, A Laboratory Manual,* 2nd edition vol. 3 (C. Nolan, ed.), Cold Spring Harbor Laboratory Press, Cold Spring Harbor, N.Y., pp. 16.30–16.81).

Differences in expression mechanisms between yeast and bacteria will most likely affect gene expression in the hybrid organism. However, it is expected that both *E. coli* and yeast will recognize the heterologous DNA unless the artificial yeast chromosome is localized, in addition to the nuclear location, within an organelle or membrane bound structure outside of the nucleus. Differences between eukaryotic and prokaryotic gene expression include the fact that transcription and translation are coupled in bacteria but occur in separate compartments in yeast. In addition, eukaryotic nuclei contain complexes of DNA, RNA, and proteins (mainly histones) in structures called chromatin, while bacteria or prokaryotes contain no such structures.

Although many metabolic pathways are shared in common by yeast and bacteria, hybrid protein-protein interactions may, in some instances, be detrimental to the function of these pathways in the hybrid organism. If there is a conflict of the two expression systems within the nucleus, an additional yeast nucleus can be introduced into the hybrid organism or cell by fusion with another yeast spheroplasts which happens during protoplast fusion. Such karyogamic yeast are stable (do not form single nucleii) mitotically unless they are exposed to a pheromone from the opposite mating type and mate to fuse nucleii. To enhance this effect, karyogamy mutants of yeast which show no nuclear fusion can be used (Marsh, L., and Rose, M. D. (1997) The pathway of cell and nuclear fusion during mating in S. cerevisiae, In *The Molecular and Cellular Biology of the Yeast Saccharomyces*, vol. 3 (E. W. Jones, J. R. Pringle, and J. R. Broach, eds.) Cold Spring Harbor Laboratory Press, pp. 827–888). There are certainly numerous concerns about deleterious interactions as well as lethality effects; therefore such yeast and bacterial hybrid organisms preferably require various selections and mutations as known in the art to obtain the desired function in the chimeric organism.

In addition to bacteria such as *E. coli*, hybrid organisms made with other prokaryotes, such as cyanobacteria (photosynthetic and nitrogen fixation pathways for yeast and other eukaryotes) ((1994); *The Molecular Biology of Cyanobacteria* vol. 1, (ed. D. A. Bryant) Kluwer Academic Publishers, Dordrecht, Boston and London), thermophilic bacteria such as thermophilic archaea (to obtain heat resistant yeast as well as other heat resistant eukaryotes), various combinations of Streptomyces (to mix antibiotic pathways in yeast) as well as other simple and complex pathways from other bacteria can be utilized and exploited. *Zymomonas mobilis* (Zhang, M., Eddy, C., Deanda, K., Finkelstein, M., Picataggio, S. (1995) Metabolic engineering of a pentose metabolism pathway in ethanologenic *Zymomonas mobilis, Science* 267:240–243) bacterium, which produces high levels of alcohol, may be used to increase alcohol production in yeast. A photosynthetic yeast may be used for the production of alcohol (for gasohol and other uses) from $CO_2$, $H_2O$, salts, and minerals using a light and dark reaction and possibly in conjunction with nitrogen fixation from atmospheric $N_2$. In this example, glycolysis would occur during the dark reaction to produce alcohol from the glucose made by the light reaction (photosynthesis). This will require a complex fermentation engineering system to maximize light and $CO_2$ uptake during exposure to light and to minimize dissolved $O_2$ in the absence of light. It will also preferably require inhibition of yeast growth during light exposure, atmospheric gas use, and $O_2$ release which could be done by putting the α factor gene into the genome of yeast using a light inducible, $O_2$ inducible, or other inducible promoter to automatically stop MATa yeast from growing during daylight hours (see references concerning yeast mating type). This would bypass the lengthy and costly process currently in use of production of the sugar by corn and the use of this corn sugar to feed yeast which then produce the alcohol. The system, described above, could be used to control the conversion of biomass (glucose) directly to alcohol in a single, light dependent organism. This could greatly reduce the cost of alcohol production for use as gasohol and also reduce pollutants and energy requirements for gasohol production. This type of hybrid yeast is preferably produced using the industrial yeasts that are employed in the existing process.

The production of AEAC-bacterial genomes for plants preferably require different telomeres, centromeres, and selectable markers that function more efficiently in plants. The transfer of bacterial genomes into plants may be used for the production of nitrogen fixing plants from ones that do not fix nitrogen. This would be especially useful for corn, rice, wheat, and other crops that take their nitrogen out of the soil. Hybrids may be made, for example, by fusing plant seed cells with various cyanobacteria protoplasts containing a pAEAC system. Azotobacter, or Rhizobium containing a pAEAC system preferably are added to plants using a gun injection technique (see above) or protoplast fusions (R. E. Kingston (1997) Electroporation into Plant Protoplasts, In *Current Protocols in Molecular Biology*, vol. 1 (F. Ausubel, R. Brent, R. Kingston, D. Moore, J. Seidman, J. Smith, and K. Struhl, eds.) John Wiley & Sons, pp. 9.3.2–9.3.3). Preferably plant protoplasts are used that can be selected and grown to produce entire plants (Rhodes, C. A., Pierce,. D. A., Mettler, I. J., Mascarenhas, D., and Detmar, J. J. (1988) Genetically transformed maize plants from protoplasts, *Science* 240:204–207). Furthermore, Rhizobium chromosomes added to the nuclei of plant legumes preferably are used to eliminate the necessity for reinfection of root cells by the whole bacterium (in itself a valuable invention). In addition, plants can be produced that have improved thermoresistance or salt tolerance by fusion of plant cells with archaebacteria containing pAEACs.

The production of AEAC-bacterial genomes for animals and human cells (AHACs) will require different telomeres, origins of replication, centromeres, and selectable markers that function in these cells to make automatic chromosomes. All of these are of similar DNA size to yeast except for the centromere which for humans is very much larger than yeast centromeres—up to several megabases compared with 125 bp for *Saccharomyces cerevisiae* (Harrington, J. J. et al. (1997) Formation of de novo centromeres and construction of first generation human artificial microchromosomes, *Nature Genetics* 15: 345–355). The centromeres are composed of repeats of 171 bp α-satellite (alphoid) DNA which have been placed together in arrays of about 1 megabase in BACs (bacterial artificial chromosomes) or cloned as arrays of around 100 kbp from chromosome parts in YACs to make artificial chromosomes in human cells (Grimes, B. and Cooke, H. (1998) Engineering mammalian chromosomes, *Human Mol. Genet.* 7: 1635–1640). These systems suggest the ability to apply our automatic artificial chromosome system to gene therapy. Gene therapy has suffered badly from delivery systems and from the low frequency of cells expressing the needed gene for the necessary length of time (Prince, H. M. (1998) Gene transfer: a review of methods and applications, Pathology 30: 335–347). AHACs carrying genomic or cDNAs for the necessary genes to be transferred would be ideal due to their formation of automatic functional chromosomes upon reaching the nuclei of the human cells. AHACs stability in bacteria (see Example 13) would allow for cost effectiveness in vesicular delivery systems (see above ref.). The use of attenuated bacteria which promote their phagocytosis into human cells, could improve AHAC delivery to, enough cells in the body. Examples of bacteria that promote their uptake into human cells are the pathogens: *Yersinia pseudotuberculosis, Shigella flexneri, Listeria monocytogenes, Salmonella typhymurium*, and *Brucella abortus* (Pizarro-Cerda, J. et al. (1997) When intracellular pathogens invade the frontiers of cell biology and immunology, *Histol. Histopathol.* 12: 1027–1038). As an alternative to using attenuated bacteria, the proteins that induce engulfment are used to make artificial membrane vesicles containing the AHAC DNA (eg. see mechanisms for Listeria: Cossart, P. (1998) Interactions of the bacterial pathogen *Listeria monocytogenes* with mammalian cells: bacterial factors, cellular ligands, and signaling, Folia Microbiol. 43: 291–303).

The following examples are offered for illustrative purposes only, and are not intended to limit the scope of the present invention in any way.

All patent and literature references cited in the present specification are hereby expressly incorporated by reference in their entirety.

EXAMPLES

Methods for bacterial growth, plasmid constructions, and transformation, except where indicated, are described in Sambrook et al. (1989) *Molecular Cloning, A Laboratory Manual*, 2nd edition, (C. Nolan, ed.) Cold Spring Harbor Laboratory Press, Cold Spring Harbor, N.Y.

Yeast growth, transformation, molecular genetics, DNA purification, vector components, *E. coli* molecular biology, DNA sequencing, and polymerase chain reaction (PCR) are described in Ausubel et al., (1997) Current protocols in molecular biology. Greene Publishing Associates and John Wiley & Sons, Inc., New York, N.Y.

*E. coli* strains used for DNA component isolation and plasmid constructions are: i) DH5α (deoR, endA1, gyrA96, hsdR17($r_K^- m_K^+$) recA1, relA1, supE44, thi-1, Δ(lacZYA-argFV169), Φ80δlacZΔM15, F-, λ-) (Hanahan. (1983) *J. Mol. Biol.* 166:557–580) and ii) 294 (F, endA, hsdR17($r_K^- m_K^+$), supE44, thi-1, relA1(?), rfbD1(?), spoT1(?), Δ(lacZYA-argFV169), Φ80δlacZΔM15, F-, λ).

*E. coli* K12 strains used for AYAC integration into bacterial chromosomes are: ER1398 {F-, endA1, hsdR2($r_K^- m_K^+$), supE44, thi-1, relA(?), rfbD1(?), spoT1(?), mcrB1-} (Kelleher and Raleigh (1991) *J. Bact.* 173:5220–5223) and NM522 {λ-, F', lacI$^q$Δ(lacZ)M15, proA+B+/supE, Δ(lac-proAB), thiΔ(hsdMS-mcrB)5, ($r_K^- m_K^+$McrBC-)} (Woodstock et al., (1989) *Nucleic Acids Res.* 17:3469–3478).

*Saccharomyces cerevisiae*, GY5325 (MATα ura3-52 trp1-Δ63 his3-Δ200 GAL) was obtained as a spore from the genetic cross of YPH499 (GY5097) (MATa ura3-52 lys2-801$_a$ ade2-101$_o$ trp1-Δ63 leu2Δ1 his3-Δ200 GAL) (Sikorski and Hieter. (1989) *Genetics* 112:19–27) with X2180-1B (MATα SUC2 mal mel gal2 CUP1) (Mortimer and Contopoulou. (1995) In *Yeast Genetic Stock Center Catalog*, 8th Edition, Dept of MCB/Division of Genetics, Univ. of Cal., Berkeley, Calif.). Yeast GY5345 (MATa ura3-52 trp1-63 ade2-101$_o$ his3-Δ200 leu2-Δ1 GAL) was obtained after a second cross of the progeny from the first cross above described which yielded GY5325. Yeast GY5328 (MATα ura3-52 trp1-Δ$^{63}$ his3-Δ200 leu2::pGAL10-HO/URA3 GAL) was generated from strain GY5325 (described above) by transformation with linear DNA which resulted in the integration of the yeast HO endonuclease gene, under the control of a galactose-inducible promoter, into the chromosomal LEU2 locus. Strain S1799D (αtrp5 his4 ade6 gal2) (Moss (1964) *Biophys. Res. Comm.* 18:850) was used for genomic DNA isolation.

DNA for Southern blots was purified from yeast using a protoplasting procedure (Ausubel et al., (1987) *Current Protocols in Molecular Biology*, vol. 2. Greene Publishing Associates and John Wiley & Sons, Inc., New York, N.Y.) in combination with a Qiagen extract and DNA purification procedure (Qiagen Plasmid Mini Handbook, Qiagen, March 1996). DNAs were digested, electrophoresed, and transferred to supported nitrocellulose (BA-S, Optitran) membranes (Schleicher and Schuell). Membranes were hybridized with biotin-labeled pBR322 DNA and visualized using the BLUEGENE nonradioactive detection system (GibcoBRL, cat. no. 18279-018, Gaithersberg, Md.).

pYAC5 was from Sigma. All commercially available products and reagents were used according to the manufacturer's protocols, except where indicated.

Example 1

Construction of an HO Endonuclease Expression System for Yeast

The following details the production of a recombinant DNA construct, GET735 (FIG. 1), that is used for the insertion by homologous recombination of the HO endonuclease gene of *S. cerevesiae* into the LEU2 locus of a haploid yeast strain (e.g. strain GY5325).

Plasmid GET735 was constructed by excising the LEU2 gene from YEp13 (Broach et al. (1979) *Gene* 8:121–123) by SalI/XhoI digestion (2.2 kbp fragment) and subcloning this fragment into the SalI site of pUC19. Two-thirds of the central portion of the LEU2 structural gene was removed by BstXI and BstEII digestion and replaced by a polylinker (BstEII)-NotI-BglII-XhoI-NheI-(BstXI) (Note: all restriction enzymes sites in parentheses are destroyed during the procedure). The URA3 (1.2 kbp) chromosomal fragment from yeast (Fasiolo et al (1981) *J. Biol. Chem.* 56:2324) was modified by addition of (HindIII)/BglII/SalI linkers and cloned into the XhoI site of the polylinker. The HO gene obtained from plasmid YCp50-HO (Herskowitz et al. (1991) *Methods in Enz.* 194:132–146) was modified by PCR at its 5' end to contain an XbaI site just 5' of the ATG initiation codon. The dual yeast promoter, GALI-10, fragment was isolated from highly expressed yeast genes by PCR of genomic DNA of yeast strain, S1799D (α trp5, his4, ade6, gal2). The PCR primers were designed to replace the ATG codons of GAL1 and GAL10 with EcoRI and BamHI sites. For HO gene expression the PCR modified HO gene was operably linked to the GAL10 side of the dual promoter and a 326 bp HindIII fragment containing the alcohol dehydrogenase I (ADHt) transcription termination region. The HO endonuclease expression cassette containing the HO endonuclease coding region operably linked to the GALI-10 promoter and alcohol dehydrogenase I transcription termination region (ADHt) was cloned into the NotI site of the polylinker adjacent to URA3, generating plasmid GE7735.

Example 2

Production of a Yeast Strain That Expresses HO Endonuclease

The purpose of this experiment is to produce a yeast strain that expresses the HO endonuclease under the control of the inducible GAL10 promoter.

Plasmid GET735 (FIG. 1, Example 1) was HpaI/SalI digested to release the fragment containing the HO endonuclease expression cassette flanked by LEU2 5' and 3' terminal sequences and URA3. Yeast strain, GY5325, was transformed with the HpaI/SalI fragment according to standard protocols. Following introduction into GY5325 and transport to the nucleus, homologous recombination mediated by the LEU2 terminal sequences results in the insertion of the HO expression cassette into the LEU2 locus of the GY5325 genome, producing strain GY5328. HO endonuclease expression was demonstrated by galactose-inducible, mating-type changes in GY5328.

Example 3

Construction of an HO and PI-SceI Restriction Recognition Sites

The purpose of this experiment is to construct plasmids containing HO and PI-SceI restriction recognition sites that will be used in the construction of automatic yeast artificial chromosome plasmids.

Figure 2:
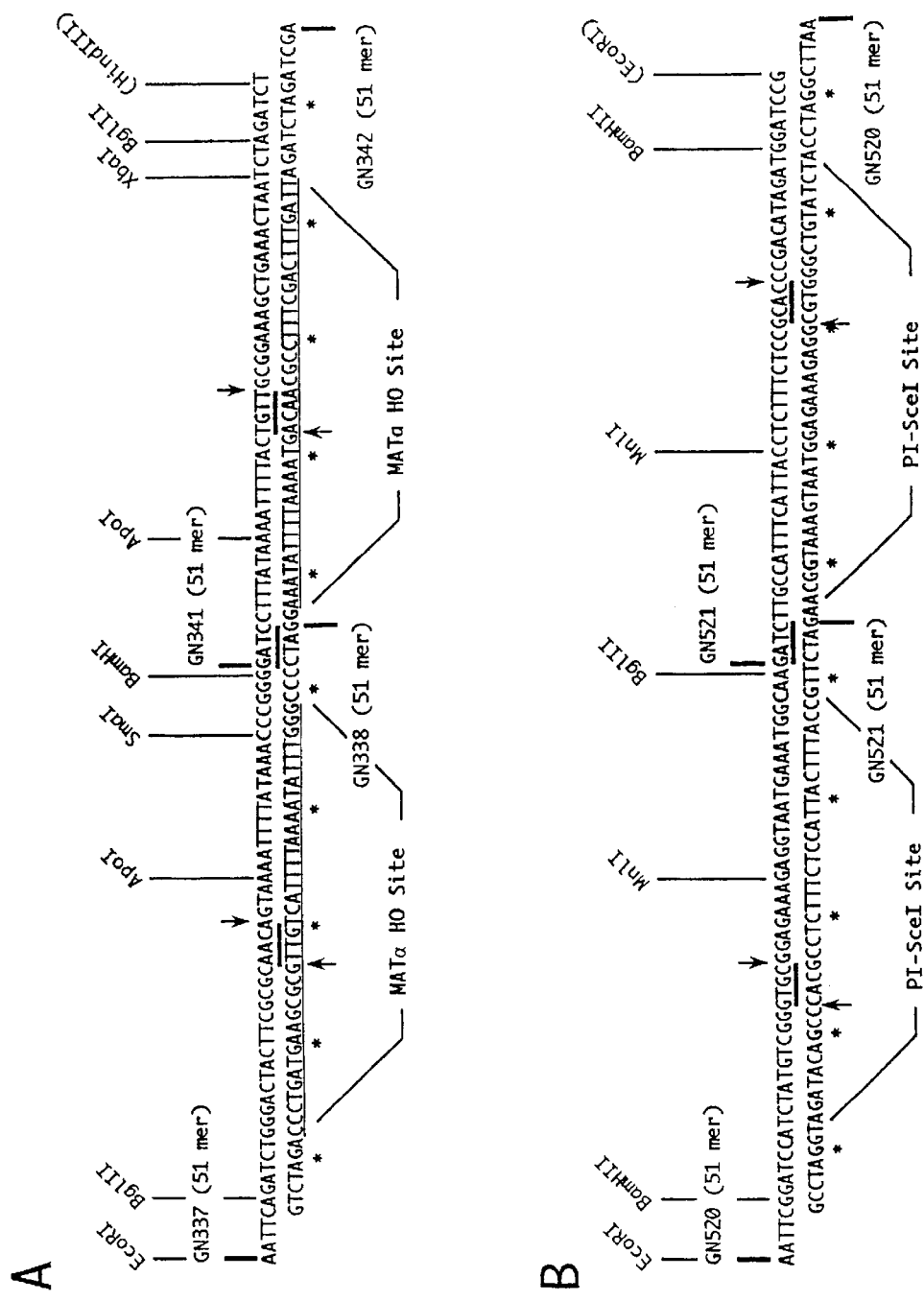
FIGS. 2A–2B show the nucleotide sequence of two synthetic dual HO sites (Panel A) (SEQ ID NOs: 1–2, DNA top and bottom strands respectively) and PI-SceI (Panel B) (SEQ ID NOs: 3–4, DNA top and bottom strands respectively) endonuclease sites. Selected restriction enzyme sites are shown. The sites of endonuclease cleavage are marked with arrows (4 bp 3' extensions for both the HO and the PI-SceI sites). GN numbers refer to the synthetic DNAs (size given in bases) used to produce the double stranded DNA. For HO sites, although only 24 bases are required for endonuclease recognition and cleavage, additional DNA up to the BglII sites is also homologous to DNA normally adjacent to the HO site in vivo.

FIG. 2A shows the MATα and MATa HO endonuclease recognition sites (Herskowitz et al. (1992) *The Molecular and Cellular Biology of the Yeast Saccharomyces*, vol 2 (Jones et al., eds) Cold Spring Harbor Laboratory Press, pp. 583–656) flanked by EcoRI and HindIII sticky ends. The non-blunt ended, double stranded DNA (FIG. 2A; SEQ ID NO:1 and SEQ ID NO:2) was formed by hybridization and ligation of 4 overlapping synthetic DNAs (GN337 (SEQ ID NO:5), GN338 (SEQ ID NO:6), GN341 (SEQ ID NO:7), and GN342 (SEQ ID NO:8) and cloned into the EcoRI and HindIII sites of pUC118. Twenty-four base pairs required for restriction digestion by the HO gene product in each site are underlined. The arrows within the recognition sequence indicates the 4-base 3' overhang produced by HO digestion.

FIG. 2B shows two PI-SceI restriction sites (Gimble, F. S., and Thorner, J,. (1993) J. Biol. Chem. 263:21844–21853) flanked by EcoRI sticky ends. The non-blunt ended, double stranded DNA (FIG. 2B; SEQ ID NO:3 and SEQ ID NO:4) was formed by annealing synthetic oligonucleotides (GN520 (SEQ ID NO:9), GN521 (SEQ ID NO:10), and cloned into the EcoRI site of pUC118. The arrows indicate the 4-base 3' overhang produced by PI-SceI endonuclease digestion.

Example 4

Construction of a pAYAC Plasmid System

The purpose of this experiment is to construct circular recombinant DNA that replicates as a linear automatic yeast artificial chromosome.

pAYAC (automatic yeast artificial chromosome plasmid; GET774) shown in FIG. 3B contains all of the components of pYAC (FIG. 3A) but also contains MATa and MATα HO endonuclease sites between the HIS3 BamHI sites adjacent to each telomere (TEL). pAYAC was made by inserting a BamHI spacer fragment which contained no BglII sites into the BamHI site between the HO restriction sites shown in FIG. 2A. The fragment shown in FIG. 2A and containing the linker was excised by BglII digestion and exchanged for the BamHI fragment of pYAC5, thereby replacing the HIS3 gene fragment. The spacer fragment was removed and replaced by the HIS3 BamHI fragment from pYAC5 to obtain pAYAC (GET774).

Example 5

Construction of a Lager pAYAC Plasmid System

Figure 3:
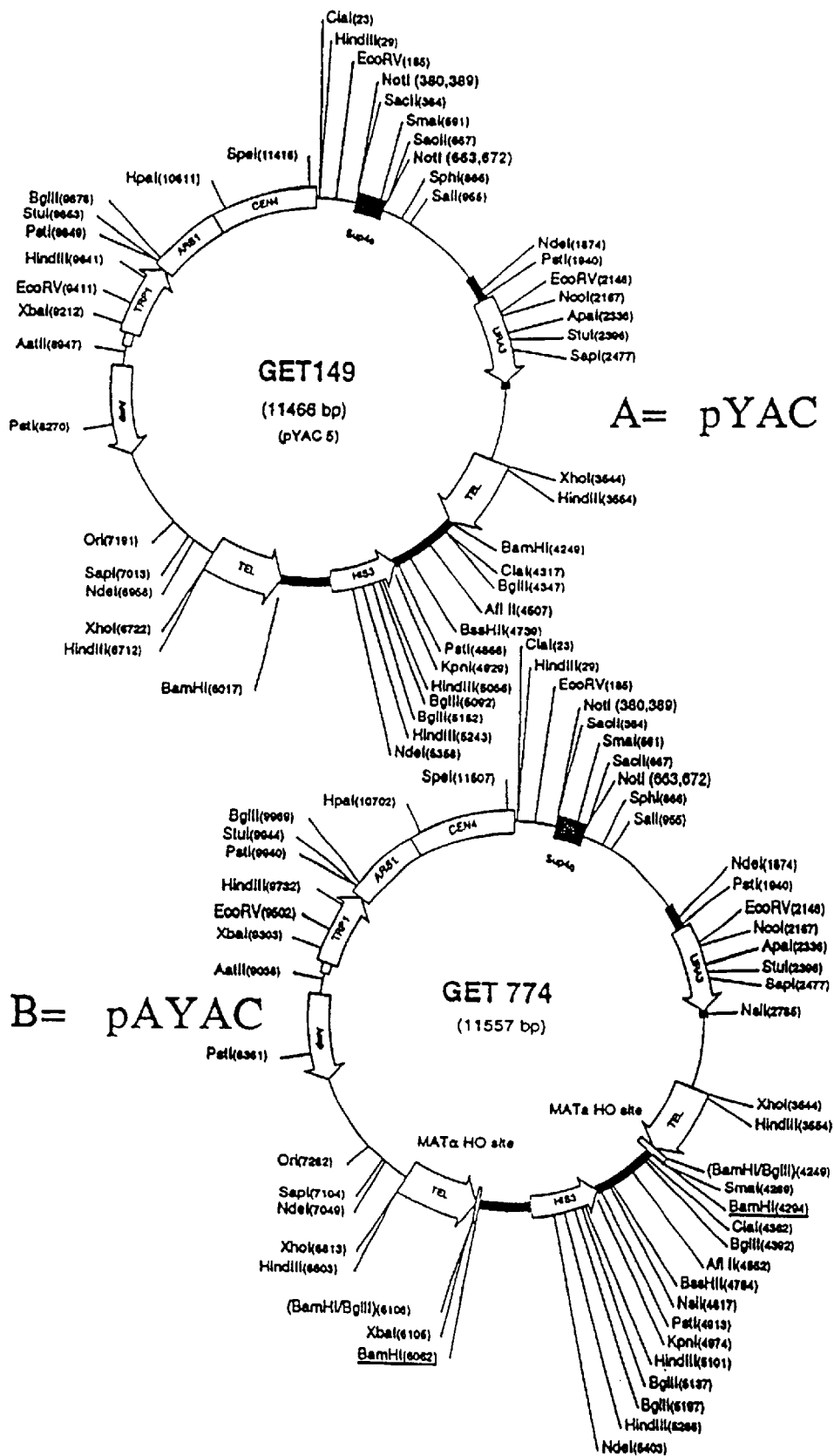
FIGS. 3A–3B show the pYAC (GET149) and pAYAC (GET774) plasmids to scale with selected restriction sites given in Panel A and Panel B, respectively. The actual size of each plasmid is given in base pairs. The white boxed-in sequences show functional units. Single lines are pBR322 sequence. Blacked boxed-in regions are yeast sequences and SUP4° is an ochre suppressor tRNA gene from yeast.

Additional DNA was inserted into the plasmids shown in FIGS. 3A–B, for the production of larger plasmids and, therefore, more stable linear artificial chromosomes (Murray, A. W., and Szostack, J. W. (1983) Construction of artificial chromosomes in yeast. *Nature* 305:189–193) after endonuclease cutting in a yeast nucleus between the two inverted telomeres.

Figure 4:
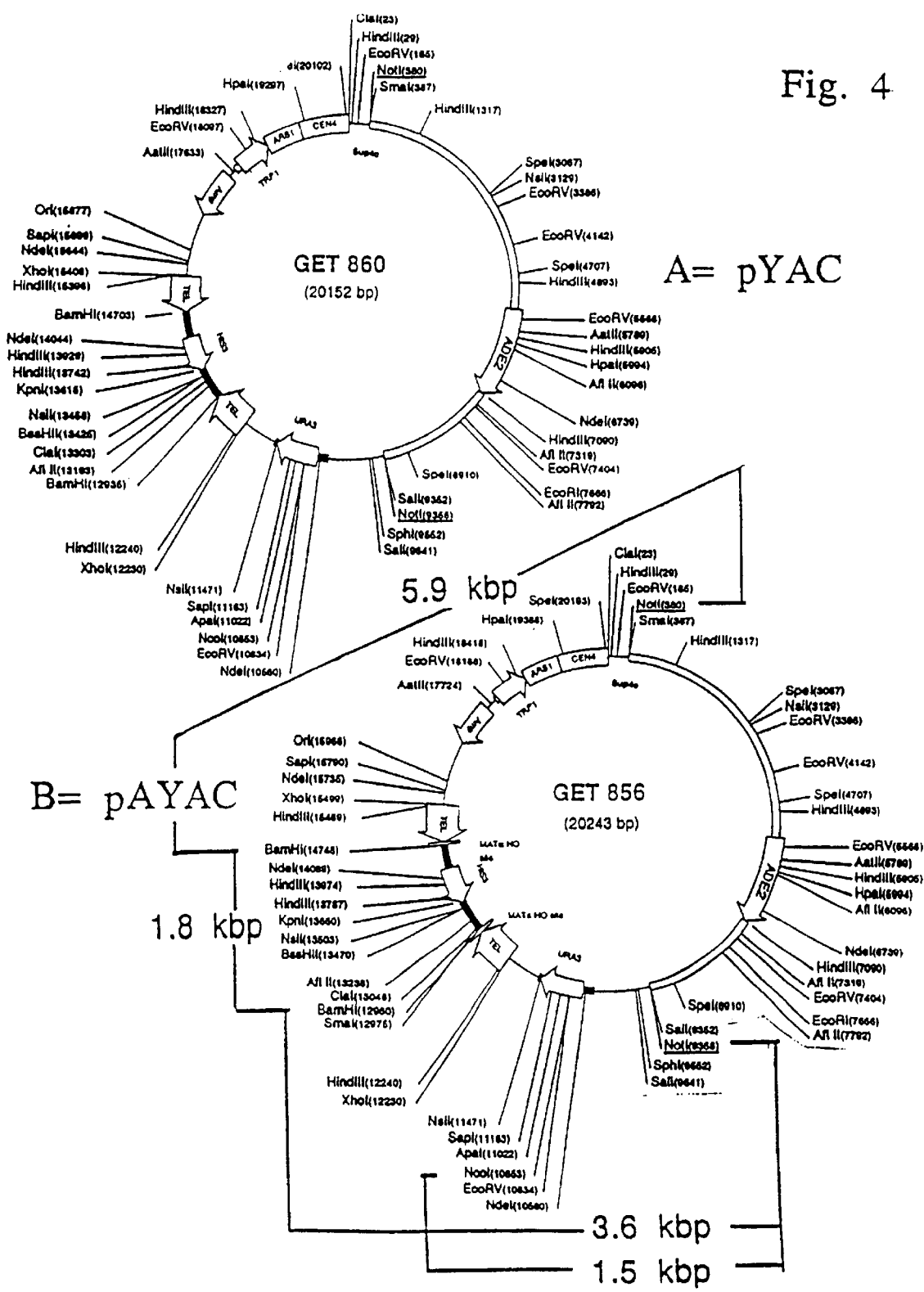
FIGS. 4A–4B show the larger pYAC (GET860)) (Panel A) and pAYAC (GET856) (Panel B) with the added yeast DNA as smaller white blocked-in regions. Yeast DNA is also shown as solid black blocks. Functional units are shown as the wide white blocks. Lines in the circular plasmid represent pBR322 DNA.

A BamHI chromosomal fragment of 8980 bp was isolated from a partial Sau3A library of S1799D (a trp5, his4, ade6 gal2) size selected genomic fragments placed in the BamHI site of plasmid YRp7 (Stinchcomb et al., (1979) *Nature* 282:39–43). Using Ade$^+$/Trp$^+$ selection (media lacking tryptophan and adenine) and strain YPH499 (MATa ura3-52 lys2-801$_a$ ade2-101$_o$ trp1-Δ63 his3-Δ200 leu2-Δ1 GAL) transformed with this pool of DNA from this genomic bank made in *E. coli*, a plasmid containing the 8980 bp fragment which contained the ADE2 gene was isolated by complementation. A BamHI 8980 bp fragment containing the yeast ADE2 gene was excised by BamHI digestion and its ends were modified by the addition of linkers to destroy the BamHI/BgnlII sites and introduce NotI sites. This DNA was ligated into the NotI sites of GET149 and GET774, producing GET860 and GET856, respectively in FIG. 4.

Example 6

Conversion of Circular Plasmids Into Linear Yeast Artificial Chromosomes

To test the for conversion of a circular plasmid into a stable linear chromosome, yeast strain GY5328 (MATα ura3-52 trp1-Δ63 his3-Δ200 leu2::pGAL10-HO/URA3 GAL) was transformed with plasmids GET149 (pYAC5, FIG. 3A), GET774 (pYAC5 with HO recognition sites. FIG. 3B), GET860 and GET856 (equivalent to GET149 and GET774, respectively, but containing an additional 8980 bp NotI fragment encoding the ADE2 gene and its adjacent chromosomal DNA, FIGS. 4A–B).

The transformed strains were selected by complementation of the tryptophan auxotrophy present in the parental strain using media containing glucose to prevent expression of the HO gene. This insures that all transformed strains contain only circular DNA at the beginning of the experiment. The conversion from circular to linear forms was initiated by incubating the transformed strains in media (0.67% Difco Yeast Nitrogen Base without amino acids (YNB)+0.5% casamino acids (CAA)) containing 2% galactose as carbon source, thereby inducing the GAL1-10 promoter and HO endonuclease expression. The transformed strains incubated in media containing 2% glucose as a carbon source served as negative controls. The transformants were incubated overnight at 30° C. in 5 ml roller cultures inoculated at an initial density of 0.1 OD600 $_{nm}$/ml. The following morning, the density of the overnight cultures was determined, the cultures were diluted to 1.0 OD600 $_{nm}$/ml and serially diluted to $10^{-4}$ at $10.2^{-2}$ increments. An aliquot (0.2 ml) of the $10^{-4}$ or final dilution of each culture, whether from glucose- or galactose-containing media, was spread onto YNB plates containing 0.5% casamino acids, histidine (36 μg/ml), 2.0% glucose, and 3% agar and incubated for 3 days at 30° C. to allow the development of isolated colonies. The phenotypes of the resulting colonies were tested by replica plating on agar plates containing only 0.67% YNB+2.0% glucose and all but one of the following additions: histidine (36 μg/ml), tryptophan (50 μg/ml), and leucine (12 μg/ml). Mating type was assessed by crossing the single colonies to strains GY5302 (MATa, lys2-801$_a$ GAL) and GY5303 (MATα lys2-801$_a$ GAL) and scoring for mating by the formation or prototrophic diploids by replication to agar plates containing only YNB and 2% glucose after an overnight incubation at 30° C. to allow mating to occur.

The results shown in Table 1 indicate that, as expected, induction of HO endonuclease by galactose growth results in mating type switching from MATα to MATa. In addition, if the transformed plasmid contains an HO endonuclease recognition site, it should be converted to a linear yeast artificial chromosome and the generation of strains that are phenotypically His$^-$ and Tip$^+$. As shown in Table 1, such colonies were generated from transformants containing either GeT774 or GET856 when utilizing galactose as carbon source. Moreover, the frequency of His$^-$ Trp$^+$ colonies increased 5.2 fold from about 0.63% to 3.3% when using the larger GET856 plasmid. No His$^-$ Trp$^+$ colonies were isolated from transformants containing GET149 or GET860 under any conditions.

Except for a population of non-mating cells, most of the cells have the parental MATα phenotype when pre-grown in medium containing glucose. However, if the same strains are pre-grown in medium containing galactose, almost complete switching of the mating phenotype is observed (mostly to MATa and more non-maters). The non-maters in the glucose grown cells might result from a low level of HO activity produced by low levels of constitutive HO expression in these strains. The increased number of non-maters in the cultures was determined spectrophotometrically at 600 nm. The cultures were diluted to 1.0 $OD_{600\ nm}$/ml and serially diluted at $10^{-2}$ increments to $10^{-4}$. A 0.2 ml aliquot of the $10^{-4}$ final dilution of each culture was spread onto duplicate YEPD-3% agar plates and incubated for 3 days at 30° C. to allow isolated colonies to develop. The phenotypes of the resulting colonies were tested by replica plating on 0.67%

TABLE 1

AYAC Plasmid Test

| Plasmid | HO Sites | Carbon Source | Total | Colony Phenotype | | | | Mating Type | | | % H−, W+ | Isolated DNA in strain GY 5345 |
|---------|----------|---------------|-------|------|------|------|-----|------|------|------|----------|---------|
|         |          |               |       | H+, W+ | H−, W− | H−, W+ | L− | MATa | MATα | None |          |         |
| GET149  | −        | Glu           | 109   | 109  | 0    | 0    | 109 | 0    | 89   | 20   | 0.00%    |         |
| "       | −        | Glu           | 124   | 124  | 0    | 0    | 124 | 0    | 99   | 25   | 0.00%    |         |
| GET774  | +        | Glu           | 106   | 106  | 0    | 0    | 106 | 0    | 93   | 13   | 0.00%    |         |
| "       | +        | Glu           | 88    | 88   | 0    | 0    | 88  | 0    | 75   | 13   | 0.00%    |         |
| GET860  | −        | Glu           | 173   | 173  | 0    | 0    | 173 | 0    | 169  | 4    | 0.00%    |         |
| "       | −        | Glu           | 128   | 128  | 0    | 0    | 128 | 0    | 119  | 9    | 0.00%    |         |
| GET856  | +        | Glu           | 148   | 148  | 0    | 0    | 148 | 0    | 138  | 10   | 0.00%    |         |
| "       | +        | Glu           | 168   | 168  | 0    | 0    | 168 | 0    | 156  | 12   | 0.00%    |         |
| GET149  | −        | Gal           | 120   | 116  | 4    | 0    | 120 | 75   | 0    | 45   | 0.00%    |         |
| "       | −        | Gal           | 85    | 85   | 0    | 0    | 85  | 63   | 2    | 20   | 0.00%    |         |
| GET774  | +        | Gal           | 238   | 234  | 1    | 2    | 238 | 177  | 5    | 56   | 0.84%    |         |
| "       | +        | Gal           | 234   | 233  | 0    | 1    | 234 | 164  | 0    | 70   | 0.43%    |         |
| GET860  | −        | Gal           | 270   | 270  | 0    | 0    | 270 | 168  | 43   | 59   | 0.00%    | GYT3678 |
| "       | −        | Gal           | 243   | 242  | 1    | 0    | 243 | 181  | 35   | 27   | 0.00%    |         |
| GET856  | +        | Gal           | 191   | 185  | 0    | 6    | 191 | 109  | 28   | 54   | 3.14%    | GYT3677 |
| "       | +        | Gal           | 202   | 195  | 0    | 7    | 202 | 116  | 38   | 48   | 3.47%    |         |

Notes
Yeast Strain GY5328
H= histidine,
W= tryptophan, and
L= lucine
None= non-mater
Glu= glucose, and
Gal= galactose galactose grown cells is expected because of the high level of mating switching and possible subsequent matings.

The phenotypes and mating types of all of the His$^-$ Trp$^+$ colonies were retested. All but one of these 16 colonies retested as His$^-$ Trp$^+$ Ura$^+$ Leu$^-$. For the 3 colonies generated from the transformants containing GET774 DNA, two were non-maters and one was MATa (all possible switched phenotypes). For the colonies derived from the transformant containing GET856 DNA there were 3 non-maters, 7 MATa and 2 MATα (10 out of 12 are possible switched phenotypes).

Example 7

Genetic Evidence for Linearity of AYAC DNA

These experiments were performed to demonstrate that plasmids containing HO endonuclease recognition sites are converted to linear AYACs following induction of the HO gene. Genetic stability and bacterial transformation efficiency were used as surrogate markers for linearity because it has been shown that circular DNA is more stable and transforms bacteria more efficiently than linear DNA.

The stability of 5 of the putative linear AYACs (His$^-$ Trp$^+$) were assessed relative to one circular pYAC (His$^+$ Trp$^+$) derived from the GET860. The colonies to be tested were grown for two days at 30° C. in rich complete YEPD medium (1% Yeast Extract, 2% Bacto Peptone and 2% glucose) in roller tube cultures. The density of the resulting YNB/0.5% casamino acids/2.0% glucose agar plates with and without tryptophan (50 μg/ml). Strains cured of extra-chromosomal DNA (either circular plasmid or linear AYAC) will have a Trp$^-$ phenotype. The circular pYAC plasmid (GET860) cured at an average rate of 3.7% while the five His$^-$ Trp$^+$ colonies derived from GET856, cured at average rates of 59.9%, 55.5%, 75.1%, 54.7%, and 55.9% respectively, consistent with an His$^-$ Trp$^+$ phenotype containing a linear chromosomal form.

Transformation efficiencies of E. coli strain DH5α were determined using DNA prepared from strains GYT3653 (derived from GY5328 transformed with GET 860, circular pYAC, FIG. 4A) and strain GYT3650 (derived from GYT5328 transformed with GET856, a putative linear AYAC, FIG. 4B). Transformation of yeast strain GY5345 (MATa trp1-Δ63 ura3-52 ade2-101$_o$ his3-Δ200 leu2-Δ1) served as a positive control. Linear DNA should not transform E. coli to ampicillin resistance but both linear and circular DNAs should transform yeast to Trp$^+$.

As expected, DNA from GYT3653 efficiently transformed E. coli while the DNA from GYT3650 generated only a few colonies (less than 5% of the number seen with GYT3653 DNA). Analysis of the plasmids contained in the E. coli transformants using restriction endonuclease digestion and agarose gel electrophoresis confirmed that all transformants from the GYT3653 DNA contained intact circular GET860 DNA while all of the transformants from GYT3650 DNA contained a plasmid that appeared to have no relationship to the pAYAC plasmids used in this study. This analysis was repeated and yielded the same results.

DNAs from GYT3653 and GYT3650 were able to transform yeast to Trp+. A slightly higher number of transformants were produced with GYT3653 DNA but it was not possible to normalize the DNA concentration prior to transformation. Phenotypic analysis of the yeast transformants indicated that all colonies were Ade+ Ura+. Colonies generated from GYT3653 DNA were also His+ while colonies generated from GYT3650 DNA were His-. These results indicate that the putative linear AYAC DNA from GYT3650 contains all the portions of the basic pYAC DNA (i.e. TRP1 URA3) in addition to the added ADE2 gene, but lacks the HIS3 gene which is removed by HO endonuclease digestion.

The E. coli transformation results suggest the possibility that the original colony containing the putative linear AYAC from GET856 (GYT3650) might also contain a low level of a contaminating circular plasmid. To test this we purified DNA from colonies generated by transforming yeast strain GY5345 with DNA from GYT3650 (GYT3677—putative linear AYAC, Table 1) and GYT3653 (GYT3678—circular GET860 control, Table 1). This DNA was used to transform E. coli strain DH5α to amplicillin resistance. Similar results to those described above were obtained and analysis of the isolated plasmids again confirmed that transformants from GYT3678 (GET860, circular control) contained intact GET860 DNA and transformants from GYT3677 (putative linear AYAC from GET856) contained a plasmid of unknown origin. DNA from both GYT3677 and GYT3678 was used to transform yeast strain GY5345 and results similar to those described above were obtained. In addition, DNA from E. coli transformants generated with GYT3677 and GYT3678 DNA was used to transform yeast strain GY5345. E. coli DNA derived from GYT3678 (GET860 circular control) was able to transform yeast to Trp+ (selection marker) and Ade+ (Ade+ and Ad- colonies are white and red, respectively). E. coli DNA derived from GYT3677 (putative linear AYAC from GET856) failed to generate Trp- colonies, suggesting that this DNA does not contain either a functional TRP1 gene or a yeast origin of replication.

Example 8

Physical Evidence for Linearity of AYAC DNA

For Southern analysis, DNA from yeast strains GYT3677 and GYT3678 (Table 1) was purified, NotI digested, electrophoresed, transferred to nitrocellulose and hybridized to a biotin-labeled probe. The Southern blot of the NotI GYT3678 DNA, FIG. 5, lane 5, yields a single band of approximately 11.3 kbp which is consistent with the transformed GET860being in a circular form. In contrast, analysis of GYT3677 DNA, FIG. 5, lane 6, yields bands of >3.6 kbp and >5.9 kbp which is the pattern expected for a linear AYAC with remodeled telomeres resulting in greater DNA fragment length.

Figure 5:
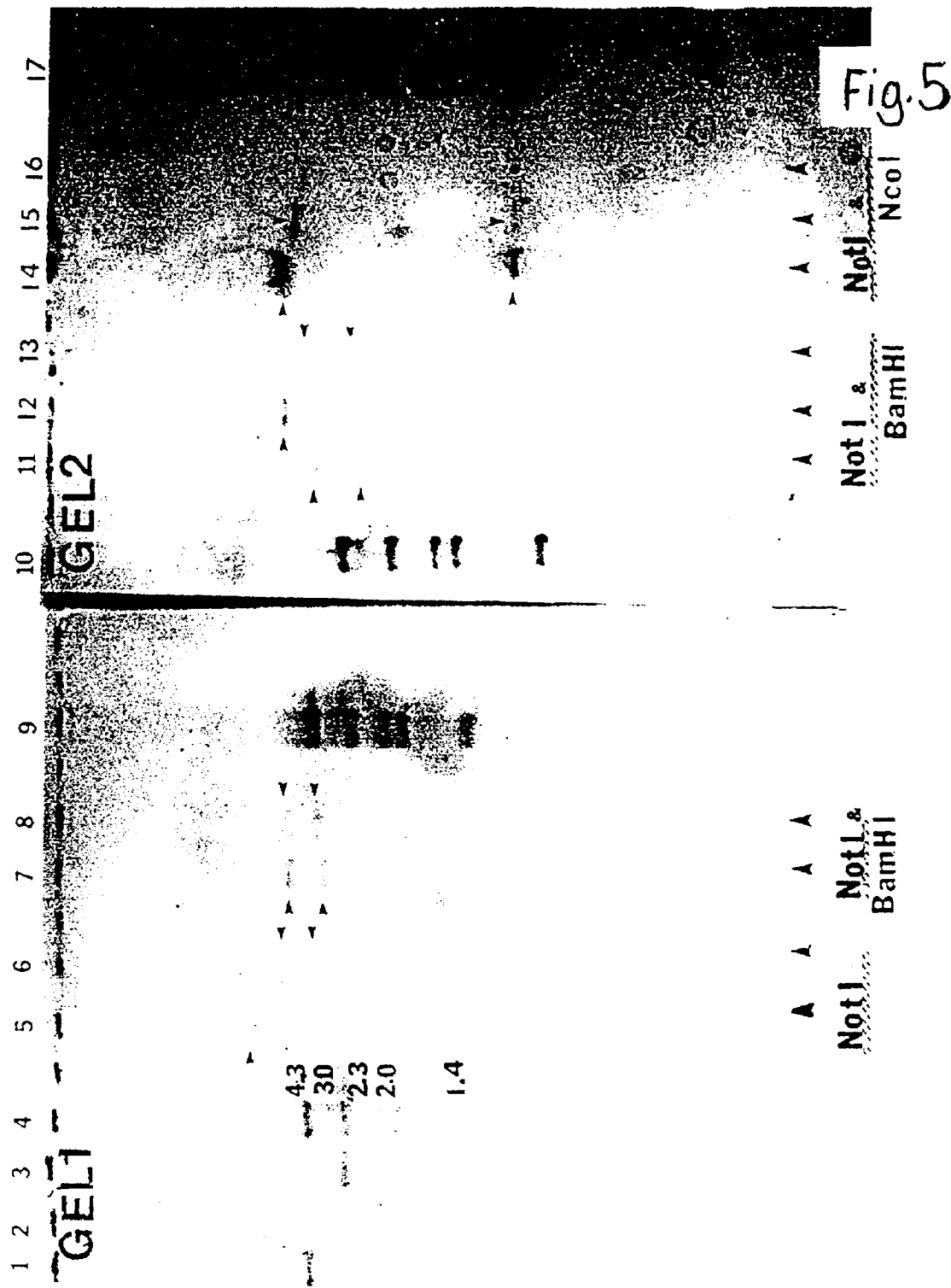
FIG. 5 shows the result of the two Southern blots using biotin detection (BLUEGENE) of bands hybridizing with pBR322 DNA that has been nick translated/biotin labeled. Various pBR322 DNA digests were used as molecular weight markers in lanes 4, 9, 10, and 17. Dark bands on the nitrocellulose correspond with DNA fragments that hybridize with the labeled probe. Lanes 5, 7, 11, and 14: GYT3678. Lanes 6 and 8: GYT3677. Lanes 12 and 15: GYT3693. Lanes 13 and 16: GYT3695. The extracted yeast DNA was restriction cut using the enzymes shown at the bottom of the gel with arrows showing which enzymes were used on the DNA in each lane. NotI/BamHI shows a combination of two restriction enzymes used. Smaller arrows designate band locations.

NotI and BamHI digestion of GYT3678 DNA yielded 3.5 kbp and 5.9 kbp fragments (FIG. 5, lane 7) due to removal of the HIS3 gene from between the two telomeres in GET860 which is expected from a circular molecule. However, NotI-BamHI digestion of GYT3677 DNA yielded the expected >3.6 kbp and >5.9 kbp fragments (FIG. 5, lane 8). This is consistent with the automatic formation of a linear AYAC in GY5328 transformed with GET856 and grown in the presence of galactose to induce HO expression. The results indicate that plasmid GET856 forms a linear AYAC in the presence of an HO endonuclease in the yeast nucleus.

Example 2

Effect of HO Recognition Site DNA on Telomere Function

This experiment was performed to evaluate the effect of the HO site DNA at the ends of the telomeres in construct GET856 on the stability of the linear AYAC DNA and to determine if the low level of His- Trp+ transformation observed after HO endonuclease induction was due to increased instability of the linear AYAC DNA caused by the HO recognition site sequences.

GET860 and GET856 DNA and were linearized by BamHI restriction endonuclease yielding identical linear AYAC molecules except for the presence of the HO endonuclease sites on the ends of the telomeres of GET856 (compare FIGS. 4A and 4B). Both linear DNAs were transformed into yeast strain GY5345. Selection for Trp+ produced only white colonies indicating co-transformation to Ade+. Several transformants for both linear DNAs were tested for stability and their phenotypes were analyzed. All the transformants were Ura+ His- as would be expected from transformation with a linear molecule. About twice as many colonies were generated from the GET856 (with HO sites) linear DNA than from the GET860 (no HO site control) but this most likely represents differences in initial DNA concentration. Transformants were scored for stability by a sectoring assay. Transformants were inoculated into YEPD medium and were grown for 48 hours at 30° C. in 5 ml roller tube cultures. The density of the resulting cultures were determined spectrophotometrically at 600 nm. The cultures were diluted to a density of 1.0 $OD_{600\ nm}$/ml and serially diluted at $10^{-2}$ increments to $10^{-4}$. A 0.2 ml aliquot of the $10^{-4}$ dilution of each culture was spread onto YEPD-3% agar plates and incubated for 3 days at 30° C. to allow colony development. Stability was assessed by scoring colony phenotype with respect to the ADE2 locus: i) colonies that had completely lost the linear AYAC were red, ii) colonies that lost the DNA after being plated on YEPD plates generated a sectored red and white colony and iii) colonies that retained the linear AYAC DNA are white.

The results of the sectoring assay is shown in Table 2. The three sections of Table 2 represent the three separate identical assays that were performed to evaluate transformant stability. As shown in Table 2, top section, the circular (Form P Table 2) control plasmids, GET860 and GET856, are very stable in strain GY5345, generating only about 1% loss in this assay. Linear (L) DNA transformants from both GET860 and GFT856 are both relatively unstable with about 10–17% loss of plasmid and 13–25% sectoring. The exception is GET856 (A) which is very stable and appears to behave like a circular molecule. Because GET856(A) is His-, this colony could not have resulted from contamination by uncut plasmid DNA in the original transformation.

Testing of additional transformants with linear AYACs yielded the following results (Table 2, middle and bottom sections). First, all transformants from linear GET860 DNA produced unstable Ade phenotypes with similar rates of sectoring (between 10 and 21%). Second, of the 8 transformants analyzed from linear GET856 DNA, 3 produced unstable Ade phenotypes while the other 5 transformants behaved like circular molecules that remained very stable in this assay. Third, the 3 unstable transformants from GET856 behaved just like all the BamHI digested GET860 DNA transformants, suggesting that the GET856 DNA is capable of forming a complete YAC just like GET860 DNA. Fourth, the data derived here further verifies the linear nature of the AYAC found in the His- Trp+ transformants generated after HO endonuclease expression identified in Table 1.

TABLE 2

Test of AYAC Linear DNAs

| DNA | Form | HO Sites | Total | Red | Sect. | % Red | % Sect. | % R + S | Ave % R + S |
|---|---|---|---|---|---|---|---|---|---|
| GET860(A) | P | − | 203 | 1 | 4 | 0.49% | 1.97% | 2.46% | |
| GET860(B) | P | − | 254 | 1 | 1 | 0.39% | 0.39% | 0.79% | |
| GET856(A) | P | + | 214 | 1 | 1 | 0.47% | 0.47% | 0.93% | |
| GET856(B) | P | + | 210 | 2 | 0 | 0.95% | 0.00% | 0.95% | |
| GET860(A) | L | − | 183 | 27 | 24 | 14.75% | 13.11% | 27.87% | |
| GET860(B) | L | − | 216 | 22 | 54 | 10.19% | 25.00% | 35.19% | |
| GET856(A) | L | + | 175 | 0 | 2 | 0.00% | 1.14% | 1.14% | |
| GET856(B) | L | + | 154 | 27 | 34 | 17.53% | 22.08% | 39.61% | |
| GET860(A) | L | − | 420 | 76 | 58 | 18.10% | 13.81% | 31.90% | 29.59% |
| " | L | − | 385 | 53 | 52 | 13.77% | 13.51% | 27.27% | |
| GET860(B) | L | − | 570 | 92 | 105 | 16.14% | 18.42% | 34.56% | 36.79% |
| " | L | − | 510 | 87 | 112 | 17.06% | 21.96% | 39.02% | |
| GET856(C) | L | + | 323 | 2 | 4 | 0.62% | 1.24% | 1.86% | 2.77% |
| (GYT3693) | L | + | 380 | 12 | 2 | 3.16% | 0.53% | 3.68% | |
| GET856(D) | L | + | 423 | 0 | 0 | 0.00% | 0.00% | 0.00% | 0.00% |
| " | L | + | 385 | 0 | 0 | 0.00% | 0.00% | 0.00% | |
| GET856(E) | L | + | 340 | 14 | 61 | 4.12% | 17.94% | 22.06% | 19.96% |
| " | L | + | 336 | 12 | 48 | 3.57% | 14.29% | 17.86% | |
| GET856(F) | L | + | 298 | 0 | 0 | 0.00% | 0.00% | 0.00% | 0.00% |
| " | L | + | 249 | 0 | 0 | 0.00% | 0.00% | 0.00% | |
| GET856(G) | L | + | 420 | 68 | 79 | 16.19% | 18.81% | 35.00% | 33.92% |
| " | L | + | 469 | 79 | 75 | 16.84% | 15.99% | 32.84% | |
| GET856(H) | L | + | 274 | 1 | 0 | 0.36% | 0.00% | 0.36% | 0.31% |
| " | L | + | 393 | 1 | 0 | 0.25% | 0.00% | 0.25% | |
| GET860(C) | L | − | 698 | 69 | 71 | 9.89% | 10.17% | 20.06% | 19.05% |
| " | L | − | 937 | 47 | 122 | 5.02% | 13.02% | 18.04% | |
| GET860(D) | L | − | 423 | 60 | 78 | 14.18% | 18.44% | 32.62% | 30.56% |
| " | L | − | 386 | 72 | 38 | 18.65% | 9.84% | 28.50% | |
| GET860(G) | L | − | 482 | 72 | 68 | 14.94% | 14.11% | 29.05% | 28.91% |
| " | L | − | 476 | 73 | 64 | 15.34% | 13.45% | 28.78% | |
| GET856(G) | L | + | 380 | 63 | 94 | 16.58% | 24.74% | 41.32% | 43.26% |
| (GYT3695) | L | + | 365 | 80 | 85 | 21.92% | 23.29% | 45.21% | |

Yeast Strain GY5345
Red= Ade⁻colony,
Sect.= Sectored Colony (Red Ade⁻ and White Ade⁺)
Form P= Plasmid,
L= Linear The generation of stable circle-like molecules from the GET856 DNA was further investigated. DNA was purified from one of the stable GET856 transformants and efficiently transformed *E. coli* to ampicillin resistance. The efficiency of the transformation was the first indication that the GET856 DNA had recircularized. Analysis of the isolated plasmid DNA, along with DNA sequencing, indicated that the GET856 DNA had recircularized and undergone a recombination event that eliminated both the HO endonuclease cleavage sites, one entire telomere and most of the second telomere.

The results of these studies indicate that the pAYAC is capable of forming a linear molecule in yeast with HO site sequences on the ends of the telomere units. However, the presence of these sequences also allows for some degree of recircularization which results in highly stable yeast transformants. However, no stable transformants were identified from the analysis of plasmid stability from the transformants generated in Table 1. This might be due to the differences in the structures of the HO recognition site sequences on the ends of the telomere units in each case; for example sites versus cleaved, partial sites. The data also suggest that the desired endonuclease cleavage site(s) are preferably placed adjacent to the telomeres with no intervening sequences to promote the most efficient formation of linear AYACs.

Lanes 10–17 of FIG. 5 show a second Southern blot with lanes 10 and 17 being pBR322 standards. GYT3678 (Table 1) as well as GYT3693 and GYT3695 (Table 2) were analyzed in lanes 11–13 and 14–16, respectively. Remember the plasmid DNAs (FIGS. 4A and 4B) from Table 2 were cut with BamHI before transformation of strain GY5345. Both can now form YACs as has been shown before (Burke et al. (1987) Cloning large DNA segments of exogenous DNA into yeast by means of artificial chromosome vectors. *Science* 236:806–812). Again GYT3678 (used on GEL1 and see Table 1) containing GET860 is again shown to be a circle when digested with NotI and BamHI giving the expected 3.6 and 5.9 kbp bands (lane 11) and when cut with NotI and NcoI giving 1.5 and 9.8 kbp bands (lane 14, also see FIG. 4). GYT3693 (Table 2) shows the cutting expected for a circular DNA that has lost the BamHI sites. This DNA is cut into 2 fragments when digested with NotI and BamHI giving one fragment at 9.5 kbp which is detected in lane 12. GYT3693 (Table 2) DNA was also digested with NotI and NcoI (see FIG. 4B) and is shown in lane 15 to contain 1.5 and 8.0 kbp fragments which hybridize with pBR322 DNA. This is consistent with it being a circular DNA lacking a BamHI site between the telomeric DNA (also based on stability). This aberrant form of GET856 transformed after digestion with BamHI is discussed earlier in the presentation of Table 2. These results suggest that complete, intact HO recognition sites on the ends of the telomeres inhibits AYAC formation. However, GYT3695 DNA (Table 2) shows the correct patterns for a properly formed linear AYAC when GET856 is BamHI digested and transformed into GY5345. BamHI and NotI digestion produced bands of >3.6 and >5.9 kbp (FIG. 5, lane 13) while NcoI and NotI digestion produced bands of >5.9, >2.1, and 1.5 kbp (FIG. 5, lane 16). Again, the fragments that are slightly larger than the expected sizes are due to remodeling of Tetrahymena telomeres after exposure of their ends in the yeast nucleus. These assays were repeated in various other yeast strains and yielded the same results (data not shown).

Example 10

Construction of Vectors for Converting a Bacterial Genome into an Automatic Yeast Artificial Chromosome FIG. 6 shows the structure of recombinant DNA plasmids designed to convert a bacterial genome into a large automatic yeast artificial chromosome plasmid (pAYAC). All four constructs contain the same backbone of functional and selectable units for expression and replication in both i) *E. coli* as either a circular plasmid or, after KpnI linearization, as an integrated DNA and ii) yeast, *Saccharomyces cerevisiae*, as either a circular plasmid or after restriction cleavage in vivo as a linear chromosome. The plasmids shown in FIG. 6 also contain bacterial target sequences, from the *E. coli* pyrD gene in this case, to allow the plasmids to be integrated into the bacterial genome. To function as pAYACs, the plasmids must also contain sites for endonuclease digestion in vivo in one of the three configurations depicted (FIG. 6, constructs #2–#4) between the telomeres. As mentioned before the "Site" in FIG. 6 is for any desired endonuclease (e.g. AMTa HO, AM Tα HO, PI-SceI, etc.) and the selectable marker can be any yeast gene (e.g. HIS3)

First pYAC5 was modified by introduction of the ClaI/SalII fragment of pBR322 encoding the tetracycline resistance gene (TetR), yielding pYAC5+Tet. The AatII/NdeI fragment containing the AmpR and a bacterial origin of replication and flanked by *E. coli* pyrD sequences was generated by first using PCR to isolate a portion of the pyrD gene of *E. coli* DH5α. The first PCR primer corresponded to nucleotides +1 to +17 (+1 being the A of the ATG initiation codon) of the pyrD gene and was designed to introduce EcoRI/AatII sites at the 5' terminus of the PCR product. The second primer corresponded to pyrD gene bases +446 to +469 and contained NdeI/HindIII sites at its 5' terminus. These two primers were used with DH5α genomic DNA to generate a fragment containing 45% of the pyrD structural gene and lacking protein coding sequence from both termini. This PCR product was cloned as an EcoRI/HindIII (455 bp) fragment in pUCI 18. An AatII/NdeI fragment from pBR322, containing the AmpR gene and an origin of replication that is functional in *E. coli*, was introduced into a unique KpnI site within the pyrD sequences (nucleotide +252). The origin of replication was previously converted to a KpnI fragment while eliminating its AatII and NdeI sites. The entire AatII/NdeI fragment (2213 bp) fragment containing the AmpR gene and replication origin flanked by pyrD sequences was exchanged into pYAC5+Tet, yielding pYAC+pyrD Ori (FIG. 6, Construct #1).

Constructs #2–#4 are identical to Construct #1 but have either one or two rare endonuclease restriction sites between the two inverted Tetrahymena telomeres. These constructs will be made by replacing the unique XhoI fragment from pYAC+pyrD Ori (Construct #1) that contains the inverted telomeres with XhoI fragments containing the desired endonuclease cleavage site structure between the telomeres.

Example 11

Conversion of a Bacterial Chromosome into an Automatic Yeast Artificial Chromosome To convert a bacterial chromosome into an automatic yeast artificial chromosome, Constructs #1–#4 (FIG. 6) will be cut with KpnI to remove the AmpR gene and *E. coli* replication origin. The remaining, larger fragment will be used to transform, for example, *E. coli* K12 strain, ER1398 {F$^-$, endA1, hsdR2($r_K^- m_K^+$), supE44, thi-1, relA?, rfbD1?, spoT1?, mcrB1$^-$} and *E. coli* K12 strain NM522 {λ$^-$-, F', lacIq Δ(lacZ)M15, proA$^+$B$^+$/supE, Δ(lac-proAB), thiΔ (hsdMS-mcrB)5, ($r_K^- m_K^-$ McrBC$^-$)} to tetracycline resistance by insertion of the entire fragment into the bacteria chromosome. Integration into the bacterial chromosomal pyrD gene by homologous recombination requires a single cross-over event. This results in the insertion of the entire fragment and a tandem duplication of two defective pyrD genes. The transformants will be Tet resistant, Ura$^-$ and Amp sensitive. The stability of the two inverted telomeres will be confirmed by PCR, using primers that hybridize to unique DNA sequences on opposite sides of the telomeres. Alternatively, a primer that hybridizes to the unique sequences of the endonuclease cleavage site used in combination with primers that hybridize to unique sequences flanking the telomere may be used.

An alternative method for integration of the pAYAC plasmid into the bacterial genome would be to use the FLIRT system (Huang, L -C., et al., (1997) Convenient and reversible site-specific targeting of exogenous DNA into a bacterial chromosome by use of the FLP recombinase: the FLIRT system. *J. Bacteriol.* 179:6076–6083). The *E. coli* pyrD target sequences would be replaced by a single 34 bp FLP recombinase recognition site (Broach, J. R. and Volkert, F. C. (1991) Circular DNA plasmids of yeasts, In *The Molecular and Cellular Biology of the Yeast Saccharomyces*, vol. 1 (E. W. Jones, J. R. Pringle and J. R. Broach, eds.) Cold Spring Harbor Laboratory Press, Cold Spring Harbor, N.Y., pp. 297–331). The pAYAC plasmid would have the bacterial origin of replication and the AmpR gene removed as above but the rest of the plasmid would be recirculated by ligation prior to transformation into the bacteria. Expression of the yeast FLP recombinase in the bacteria would result in the integration of the pAYAC into the bacterial genome which also would contain a single 34 bp FRT recombination site. This site could be introduced by the use of a transposon as described for the FLIRT system or could be integrated into the phage lambda attachment site using the lambda integrase gene product Yeast strains GY5328 (HO endonuclease gene under galactose control, MATα ura3-52 trp1-Δ63 his3-Δ200 leu2::pGAL10 -HO/URA3 GAL) and GY5097 (YPH499= MATa ura3-52 lys2-801$_a$ ade2-101$_o$ trp1-Δ63 his3-Δ200 leu2-Δ1 GAL) have been made rho° (essentially no mitochondrial DNA or functional mitochondria) using a standard ethidium bromide procedure (Fox, T. D., Folley, L. S., Mulero, J. J., McMullin, T. W., Thorsness, P. E., Hedin, L. O., and Costanzo, M. C. (1991) Analysis and manipulation of yeast mitochondrial genes, *Methods of Enzymol.* 194: 149–165). These strains will be converted into protoplasts by removing the cell wall using zymolyase instead of glusulase as described in the reference concerning yeast transformation (Lundblad, V. (1997) *Saccharomyces cerevisiae* In *Current Protocols in Molecular Biology* vol. 2 (F. Ausubel, R. Brent, R. Kingston, D. Moore, J. Seidman, J. Smith, and K. Struhl, eds.) John Wiley & Sons, pp.13.0.1–13.14.17). The *E. coli* transformants containing the modified chromosome will be spheroplasted using either ampicillin or lysozyme (Sambrook, J., Fritsch, E. F., and Maniatis, T. (1989) Introduction of recombinant vectors into mammalian cells. In *Molecular Cloning, A Laboratory Manual,* 2nd edition vol. 3 (C. Nolan, ed.), Cold Spring Harbor Laboratory Press, Cold Spring Harbor, N.Y., pp.

16.30–16.81). The yeast protoplasts and bacterial spheroplasts will be fused at a ratio of 100 1000 bacteria per yeast as described in Curran, B. P., and Bugeja, V. C. (1996) Protoplast fusion in *Saccharomyces cerevisiae.*, In *Methods in Molecular Biology, Yeast Protocols*, vol. 53 (I. Evans, ed.), Humana Press, Inc., Totowa, N.J., pp.45–49.

Transformed yeast will be selected by the conversion from a Trp$^-$, Ura$^-$ phenotype to a Trp$^+$, Ura$^+$ phenotype. If the endonuclease site used in the pAYAC is PI-SceI, then the conversion from circular plasmid to linear chromosome will occur immediately in either yeast strain above since PI-SceI endonuclease is constituvely expressed in most yeast strains. In order to induce linearization of the pAYAC containing HO endonuclease sites, the transformation medium will have to contain galactose in order to induce HO endonuclease expression in strain GY5328. In either case, Construct #1 integrants (FIG. 6), would not be expected to generate many, Trp$^+$, Ura$^+$transformants since there is no way this construct can be converted to a linear molecule because it contains no endonuclease site between the telomeres. The intact, circular molecule would not be expected to be stable because to it's large size, now about 4.7 Mbp due to the presence of the bacterial genome. If Construct #4 integrants are used, then conversion to a linear chromosome could be monitored by testing for the loss of the selectable marker (HIS3 in the example given in FIG. 6) positioned between the endonuclease cleavage sites.

Example 12

Analysis of Bacterial Genomes Converted into Automatic Yeast Artificial Chromosomes The conversion of a bacterial genome into a linear AYAC will result in a DNA of approximately 4.7 Mbp. This molecule is about twice the size of the largest yeast chromosome (2 Mbp) and can be detected as a linear molecule by CHEF or pulsed-field electrophoresis as described by Birren, B., and Lai, E. (1993) *Pulsed Field Gel Electrophoresis*, Academic Press, Inc., Harcourt and Jovanovich, publishers, San Diego, Calif.

Growth of the yeast-bacteria fusions on xylose will be used as a functional test for expression of the bacterial genes because the yeast genome lacks the genes required for growth on xylose. Alternatively, complementation of the yeast markers lys2-801$_a$, ade2-101$_o$, his3-Δ200, leu2-Δ1 the bacterial genome will be checked.

Growth of Trp$^+$ 0and Ura$^+$ transformants containing AYACs on 2% glycerol and 2% ethanol will be used to determine if introduction of the bacterial genome converts the yeast to Rho$^+$. This would demonstrate that mitochondrial function has been restored by expression of the bacterial genome. Using Constructs #2–#4 in FIG. 6, Trp complementation by AYAC formation in the yeast nucleus will also be selected for at the same time as complementation of microchondrial function. An additional method to demonstrate restoration of mitochondrial function by the bacterial DNA include altered sensitivity to various antibiotics (as already discussed).

Example 13

Two Types of AEACs Constructed in Bacteria for Function in Eukaryotes Other Than Yeast In a similar manner to the automatic yeast artificial chromosome construction and formation already discussed, two types of AEACs are shown in FIG. 7. The functional components on this figure are general and are not to scale.

The top of FIG. 7 shows a system similar to that shown in FIG. 6: a general system for all other eukaryotes where the prokaryotic genome is to be included in the AEAC for possible function. Here the two telomeres have the rare endonuclease recognition site between two inverted telomeres that function in the chosen eukaryote after cleavage in the nucleus of the eukaryote. An example of this type of construction would be in nitrogen fixing bacteria for use in plants to obtain nitrogen fixation as a permanent genetic trait in legumes and in non legumes (e.g. corn, wheat, and rice) as previously discussed. Prokaryotic and eukaryotic components must function in the chosen prokaryote and eukaryote that are to be used for AEAC construction and application. The eukaryotic origin(s) of replication are functionally required but are generally found throughout the prokaryotic and eukaryotic DNAs on the AEAC instead of localized as shown (also true for System B, FIG. 7). As in human cells the centromeres for plants are very large. The centromeres of the plant *Arabidopsis thaliana* appear to be very similar to human centromeres since they consist of up to a 1 Mbp region consisting of 180 bp repeated units (Round, E. K. et al. (1997) *Arabidopsis thaliana* centromere regions: genetic map positions and repetitive DNA structure, *Genome Research* 7:1045–1053). Other plants contain similar repeated DNAs as centromeres. Cloning of these regions with flanking DNA as shown in FIG. 7 preferably require unique restriction sites in flanking DNA containing genes, the addition of homologous flanking DNA to the bacteria genome prior to integration of the centromeric DNA, and the addition of an additional prokaryotic selectable marker between one flanking sequence and the centromere. However, as with human centromeres, plant centromeres may be able to be constructed artificially (Grimes, B., and Cooke, H. (1998) *Human Mol. Genet.* 7:1635–1640). The endonuclease that cleaves between the telomeres is produced by a promoter and terminator that functions in the plant and may require a nuclear localization signal to direct it to the plant nucleus.

System B (at the bottom of FIG. 7) differs from System A in that the telomeres with two adjacent endonuclease recognition sites are separated by the bacterial DNA. Thus, upon cleavage in the nucleus of the eukaryote, the bacterial genomic DNA is lost from the AEAC and is not incorporated into the eukaryotic genome. An potential use for this system would be to carry functional genes to replace inactive genes for gene therapy in humans. Here again a centromere that functions in human cells is very large and may be added as a natural centromere or as an artificial human centromere (Grimes, B., and Cooke, H. (1998) *Human Mol. Genet.* 7:1635–1640). Telomeres that function in human cells can be made using PCR and an example of a human selectable marker is βgeo (Harrington, J. J. et al. (1997) *Nature Genetics* 15:345–355).

Integrations into the bacterial genomes of both systems and the placement of the bacteria carrying the AEACs into eukaryotic cells would generally be as described for *E. coli* and the AYAC system; however, dealing with large centromeres requires agarose plug handling and pulsed field gel electrophoresis of DNAs (Harrington, J. J. et al. (1997) *Nature Genetics* 15:345–355).

The foregoing written specification is considered to be sufficient to enable one skilled in the art to practice the invention over its entire range of scope. The present invention is not to be limited in scope by specific embodiments, which are intended as single illustrations of certain aspects of the invention. Further, any embodiments that are functionally equivalent are within the scope of this invention. It is also not to be construed that the scope of the claims is limited to the specific illustrations that are represented. Indeed, various modifications of the invention in addition to those shown and described herein will become apparent to those skilled in the art from the foregoing description and are intended to fall within the scope of the appended claims.

What is claimed is:

1. An automatic eukaryotic artificial chromosome vector comprising:
   (a) a prokaryotic selectable marker(s);
   (b) a DNA sequence selected from the group consisting of a DNA encoding a eukaryotic selectable marker(s), eukaryotic gene(s), eukaryotic cDNA(s), and combinations thereof;
   (c) a centromere;
   (d) a eukaryotic replication sequence(s);
   (e) at least two inverted telomeres;
   (f) restriction endonuclease site(s) at the functional chromosomal end of each telomere, wherein restriction at said site(s) converts said inverted telomeres into functional telomeres; and
   (g) a prokaryotic genome.

2. The automatic eukaryotic artificial chromosome vector according to claim 1 wherein said centromere, replication sequence(s), and telomeres function in a cell of an animal, plant, fungus, or a Protist.

3. The automatic eukaryotic artificial chromosome vector according to claim 1, wherein said centromere, replication sequence(s), and telomeres function in yeast.

4. The automatic eukaryotic artificial chromosome vector according to claim 1, wherein said restriction endonuclease site(s) are selected from the group consisting of an HO site, a PI-SceI site, and any other site of a member of a class of very rare cutting restriction endonucleases.

5. A method of converting an automatic eukaryotic artificial chromosome vector into a eukaryotic artificial chromosome comprising: fusing a prokaryote with a eukaryotic cell, wherein said prokaryote comprises an automatic eukaryotic artificial chromosome vector comprising,
   (a) a prokaryotic selectable marker(s);
   (b) a DNA sequence selected from the group consisting of a DNA encoding a eukaryotic selectable marker(s), eukaryotic gene(s), eukaryotic cDNA(s), and combinations thereof;
   (c) a centromere;
   (d) a eukaryotic replication sequence(s);
   (e) at least two inverted telomeres;
   (f) restriction endonuclease site(s) at the functional chromosomal end of each telomere; and
   (g) optionally comprising at least a portion of a prokaryotic genome,
   wherein said eukaryotic cell expresses restriction endonuclease(s) that restricts said vector at said site(s), whereby said vector is converted into a eukaryotic artificial chromosome.

6. The method according to claim 5 whereby said cell acquires an altered phenotype.

7. The method according to claim 5, wherein said eukaryotic cell is an animal, plant, fungus, or Protist cell.

8. The method according to claim 7, wherein said fungus cell is a yeast cell.

9. The method according to claim 5, wherein said prokaryote is an archaebacterium, a eubacterium, *Escherichia coli*, cyanobacterium, Azotobacter, Rhizobium, a photosynthetic bacterium, a nitrogen fixing bacterium, a thermophilic bacterium, or an antibiotic producing bacterium.

10. The vector according to claim 1, wherein said prokaryotic genome is an archaebacterium, a eubacterium, *Escherichia coli*, cyanobacterium, Azotobacter, Rhizobium, a photosynthetic bacterium, a nitrogen fixing bacterium, a thermophilic bacterium, or an antibiotic producing genome.

11. The method according to claim 9 wherein said antibiotic producing genome is a Streptomyces genome.

12. A method of altering a phenotype of a eukaryotic cell comprising: fusing a first prokaryote and a second prokaryote with a eukaryotic cell, wherein at least one of said prokaryotes comprises an automatic eukaryotic chromosome vector comprising, (a) a prokaryotic selectable marker(s);

(b) a DNA sequence selected from the group consisting of a DNA encoding a eukaryotic selectable marker(s), eukaryotic gene(s), eukaryotic cDNA(s), and combinations thereof;

(c) a centromere;

(d) a eukaryotic replication sequence(s);

(e) at least two inverted telomeres;

(f) restriction endonuclease site(s) at the functional chromosomal end of each telomere; and (g) optionally comprising at least a portion of a prokaryotic genome, whereby said eukaryotic cell acquires an altered phenotype.

13. The method according to claim 6 further comprising selecting for said eukaryotic cell comprising said altered phenotype.

14. The method according to claim 6, wherein said altered phenotype is selected from the group consisting of modified expression of a gene, photosynthesis, ethanol synthesis, and nitrogen fixation.

15. The method according to claim 6, wherein said vector comprises a prokaryotic genome.

16. The method according to claim 12, whereby said first or second prokaryote is converted into an organelle of said eukaryotic cell.

17. The method according to claim 12, whereby said vector is converted into a eukaryotic artificial chromosome.

18. A method of converting an automatic eukaryotic artificial chromosome vector into a eukaryotic artificial chromosome comprising: fusing a prokaryote with a eukaryotic cell, wherein said prokaryote comprises an automatic eukaryotic artificial chromosome vector comprising, (a) a prokaryotic selectable marker(s);

(b) a DNA sequence selected from the group consisting of a DNA encoding a eukaryotic selectable marker(s), eukaryotic gene(s), eukaryotic cDNA(s), and combinations thereof;

(c) a centromere;

(d) a eukaryotic replication sequence(s);

(e) at least two inverted telomeres;

(f) restriction endonuclease site(s) at the functional chromosomal end of each telomere; and (g) optionally comprising at least a portion of a prokaryotic genome, whereby said vector is converted into a eukaryotic artificial chromosome.

19. A method of converting an automatic eukaryotic artificial chromosome vector into an eukaryotic artificial chromosome comprising: restricting an automatic eukaryotic artificial chromosome vector, wherein said vector comprises, (a) a prokaryotic selectable marker(s);

(b) a DNA sequence selected from the group consisting of a DNA encoding a eukaryotic selectable marker(s), eukaryotic gene(s), eukaryotic cDNA(s), and combinations thereof;

(c) a centromere;

(d) a eukaryotic replication sequence(s);

(e) at least two inverted telomeres;

(f) restriction endonuclease site(s) at the functional chromosomal end of each telomere; and (g) a prokaryotic genome, whereby said restricting at said sites said vector is converted into a eukaryotic artificial chromosome.

20. The method according to claim 19, wherein said genome is flanked by said restriction endonuclease sites.

21. The method according to claim 12 further comprising selecting for said eukaryotic cell comprising said altered phenotype.

22. The method according to claim 12, wherein said altered phenotype is selected from the group consisting of modified expression of a gene, photosynthesis, ethanol synthesis, and nitrogen fixation.

23. The method according to claim 12, wherein said vector comprises a prokaryotic genome.

* * * * *

UNITED STATES PATENT AND TRADEMARK OFFICE
CERTIFICATE OF CORRECTION

PATENT NO.      : 6,670,154 B1
DATED           : December 30, 2003
INVENTOR(S)     : Ronald A. Hitzeman and George E. Chisholm, IV It is certified that error appears in the above-identified patent and that said Letters Patent is hereby corrected as shown below:

Title page,
Item [56], References Cited, OTHER PUBLICATIONS, replace "Mar. 1991" with -- Mar. 1981 --; and replace "Vacterial Chromosome" with -- Bacterial Chromosome --

Column 1,
Line 63, replace "norm" with -- norm- --

Column 2,
Line 23, replace "LEU2" with -- $LEU2$ --
Lines 24-25, replace "LEU2 3' region, URA3 promoter and terminator, and the HO restriction" with -- $LEU2$ 3' region, $URA3$ promoter and terminator, and the $HO$ restriction --
Lines 29, 37 and 40, replace "HO" with -- $HO$ --
Line 30, replace "PI-SceI" with -- PI-$SceI$ --
Lines 34-35, replace "HO and the PI-SceI" with -- $HO$ and the PI-$SceI$ --
Line 39, replace "BglII" with -- Bg/II --
Line 47, replace "SUP4$^o$" with -- $SUP4^o$ --
Linhe 48, replace "pYAC (GET860))" with -- pYAC(GET860) --
Line 65, replace "NotI/BamHI" with -- $NotI$/$Bam$HI --

Column 3,
Line 1, replace "pyrD" with -- $pyrD$ --
Lines 7-8, replace "MATαHO, MATαHO, PI-SceI" with -- $MATaHO$, $MATαHO$, PI-$SceI$ --
Line 9, replace "HIS3" with -- $HIS3$ --
Line 27, replace "in vivo" with -- $in\ vivo$ --

Column 4,
Line 16, replace "Tetrahymena" with -- Tetrahymena --
Line 59, replace "in vitro" with -- $in\ vitro$ --
Line 61, replace "in vivo" with -- $in\ vivo$ --
Line 65, replace "rho⁻ or rho°" with -- $rho^-$ or $rho^o$ --
Line 66, replace "mitochrondrial" with -- mitochondrial --

Column 5 ,
Line 16, replace "in vitro" with -- $in\ vitro$ --
Lines 46-48, replace "Azotobacter, Rhizobium, Streptomyces, Synechococcus PCC6301, and Anabaena" with -- $Azotobacter,\ Rhizobium,\ Streptomyces,\ Synechococcus$ PCC6301, $and\ Anabaena$ --
Lines 54-55, replace "HO (24bp), SceI (18bp), and PI-SceI (31bp)." with -- $HO$ (24 bp), I-$SceI$ (18 bp), and PI-$SceI$ (31 bp). --

UNITED STATES PATENT AND TRADEMARK OFFICE
CERTIFICATE OF CORRECTION

PATENT NO. : 6,670,154 B1
DATED : December 30, 2003
INVENTOR(S) : Ronald A. Hitzeman and George E. Chisholm, IV It is certified that error appears in the above-identified patent and that said Letters Patent is hereby corrected as shown below:

Column 5, cont'd.,
Lines 60, 62 and 66, replace "HO" with -- *HO* --
Line 61, replace "site it thought" with -- site is thought --
Line 63, replace "recA⁻ *E. coli* cells, recA⁺" with -- *recA*⁻ *E. coli* cells, *recA*⁺ --
Line 65, replace "recA" with -- *recA* --

Column 6,
Lines 2, 3, 4, 5, 12, 14, 36, 45 and 48, replace "HO" with -- *HO* --
Lines 2, 3 and 37, replace "MAT" with -- *MAT* --
Lines 5 and 6, replace "in vitro" with -- *in vitro* --
Lines 5 and 12, replace " in vivo" with -- *in vivo* --
Lines 14, 23 and 24, replace "SceI" with -- *Sce*I --
Line 59, replace "*E. Coli*" with -- *E. coli* --

Column 7,
Line 27, replace "TRPI and URA3" with -- *TRPI* and *URA3* --
Lines 41 and 60, replace "rho⁻ and rho⁰" with -- *rho*⁻ and *rho*⁰ --
Line 44, replace "rho⁰" with -- *rho*⁰ --

Column 8,
Line 23, replace "Rassoulzadegan" with -- (Rassoulzadegan --
Line 28, replace "(dam, the Sau3AI, and the SssI" with -- *(dam,* the *Sau*3AI, and the *Sss*I --
Line 31, replace "in vivo" with -- *in vivo* --

Column 9,
Line 1, replace "spheroplasts" with -- spheroplast --
Line 25, replace "Streptomyces" with -- *Streptomyces* --
Line 47, replace "MATa" with -- *MAT*a --

Column 10,
Line 2, replace "Azotobacter, or Rhizobium" with -- *Azotobacter or Rhizobium* --
Line 13, replace "Rhizobium" with -- *Rhizobium* --
Line 51, replace "to," with -- to --

UNITED STATES PATENT AND TRADEMARK OFFICE
CERTIFICATE OF CORRECTION

PATENT NO. : 6,670,154 B1
DATED : December 30, 2003
INVENTOR(S) : Ronald A. Hitzeman and George E. Chisholm, IV It is certified that error appears in the above-identified patent and that said Letters Patent is hereby corrected as shown below:

Column 11,
Lines 14-15, replace "Current Protocols in Molecular Biology" with -- *Current Protocols in Molecular Biology* --
Lines 18-21, replace "deoR, endAl, gyrA96, hsdR17($r_K^-$ $m_K$+) recA1, relA1, supE44, thi-1, Δ(lacZYA-argFV169), Φ80δ1acZ ΔM 15, F⁻" with -- *deoR, endAl, gyrA96, hsdR17($r_K^-$ $m_K$+) recAl, relAl, supE44, thi-1, Δ(lacZYA-argFV169), Φ80δ1acZΔM15, F⁻* --
Lines 22-24, replace "F, endA, hsdR17($r_K^-$ $m_K^+$), supE44, thi-1, relA1(?), rfbDl(?), spoTl(?), Δ(lacZYA-argFV169), Φ80δ1acZΔM15, F⁻" with -- *F, endA, hsdR17($r_K^-$ $m_K^+$), supE44, thi-1, relAl(?), rfbDl(?), spoTl(?), Δ(lacZYA-argFV169), Φ80δ1acZΔM15, F⁻* --
Lines 26-27, replace "F⁻, endA1, hsdR2($r_K^-$ $m_K^+$), supE44, thi-1, relA(?), rfbDl(?), spoTl(?), mcrBl⁻" with -- *F⁻, endA1, hsdR2($r_K^-$ $m_K^+$), supE44, thi-1, relA(?), rfbDl(?), spoTl(?), mcrBl⁻* --
Lines 28-29, replace "F', lacI$^q$Δ(lacZ)M15, proA⁺B⁺/supE, Δ(lac-proAB), thiΔ(hsdMS-mcrB)5" with -- *F', lacI$^q$Δ(lacZ)M15, proA⁺B⁺/supE, Δ(lac-proAB), thiΔ(hsdMS-mcrB)5* --
Lines 33-34, replace "MATα ura3-52 tri l-Δ63 his3-Δ200 GAL" with -- *MATα ura3-52 trp l-Δ63 his3-Δ200 GAL* --
Lines 35-36, replace "MATa ura3-52 lys2-801$_α$ ade2-101$_o$ trp1-Δ63 leu2Δ1 his3-Δ200 GAL" with -- *MATa ura3-52 lys2-801$_α$ ade2-101$_o$ trp1-Δ63 leu2Δ1 his3-Δ200 GAL* --
Line 38, replace "MATα SUC2 mal mel gal2 CUP1" with -- *MATα SUC2 mal mel gal2 CUP1* --
Line 39, replace "In" with -- *In* --
Lines 41-42, replace "MATa ura3-52 trp1-63 ade2-101$_o$ his3-Δ200 leu2-Δl GAL" with -- *MATa ura3-52 trp1-Δ63 ade2-101$_o$ his3-Δ200 leu2-Δl GAL* --
Lines 44-46, replace "MATα ura3-52 trp1-Δ$^{63}$ his3-Δ200 leu2::pGAL 10-HO/URA3 GAL" with -- *MATα ura3-52 trp1-Δ63 his3-Δ200 leu2*::pGAL10-HO/*URA3* GAL --
Line 48, replace "HO" with -- *HO* --
Line 50,
Line 50, replace "LEU2 locus. Strain S1799D (αtrp5 his4 ade6 ga12)" with -- *LEU2* locus. Strain S 1799D (α *trp5 his4 ade6 gal2*) --

Column 12,
Lines 2, 7, 21, 22, 30 (both occurrences), 33, 34, 42, 45, 48, 55, 56, 61, and 65, replace "HO" with -- *HO* --
Lines 8, 10, 14, 49, 54, and 55 replace "LEU2" with -- *LEU2* --
Line 12, replace "Sal1/XhoI" with -- *Sal*I/*Xho*I --
Line 13, replace "Sall" with -- *Sal*l --
Line 15, replace "BstXI and BstEII" with -- *Bst*XI and B*st*EII --
Line 16, replace "(BstEII)-NotI-Bg1II-XhoI-NheI-(BstXI)" with -- (*Bst*EII)-*Not*I-*Bgl*II *Xho*I-*Nhe*I-(*Bst*XI) --

UNITED STATES PATENT AND TRADEMARK OFFICE
CERTIFICATE OF CORRECTION

PATENT NO. : 6,670,154 B1
DATED : December 30, 2003
INVENTOR(S) : Ronald A. Hitzeman and George E. Chisholm, IV It is certified that error appears in the above-identified patent and that said Letters Patent is hereby corrected as shown below:

Column 12 cont'd.,
Lines 18, 38, and 50, replace "URA3" with -- *URA3* --
Line 20, replace "HindIII)BglII/SalI" with -- *Hind*III)/*Bgl*II/*Sal*I --
Line 21, replace "XhoI" with -- *Xho*I --
Line 24, replace "XbaI" with -- *Xba*I --
Lines 27-28, replace "trp5, his4, ade6, gal2" with -- *trp5, his4, ade6, gal2* --
Line 29, replace "GAL1 and GAL10 with EcoRl and BamHI" with -- *GAL1* and *GAL10* with *Eco*RI and *Bam*HI --
Line 32, replace "HindIII" with -- *Hind*III --
Line 37, replace "NotI" with -- *Not*I --
Lines 47 and 51, replace "HpaI/SalI" with -- *Hpa*I/*Sal*I --
Lines 61 and 65, replace "SceI" with -- *Sce*I --

Column 13,
Lines 1 and 34, replace "MATα and MATa HO" with -- *MAT*α and *MAT*a *HO* --
Lines 5, 10, 17 and 21, replace "EcoRI" with -- *Eco*RI --
Lines 5 and 11, replace "HindIII" with -- *Hind*III --
Lines 12, 14 and 38, replace "HO" with -- *HO* --
Lines 15 and 22, replace "PI-SceI" with -- PI-*Sce*I --
Lines 35, 41 and 43, replace "HIS3" with -- *HIS3* --
Lines 35, 37, 38, 41, 43, 56, 58, 66 and 67, replace "BamHI" with -- *Bam*HI --
Lines 37, replace "BglII" with -- *Bgl*II --
Line 40, replace "BglII digestion" with -- *Bgl*II digestion --
Line 57, replace "Sau3A" with -- *Sau*3A --
Line 57-58, replace "a trp5, his4, ade6 gal2" with -- α *trp5, his4, ade6 gal2* --
Line 59, replace "et al" with -- *et al* --
Lines 61-62, replace "MATa ura3-52 lys2-801$_a$ ade2-101$_o$ trp1-Δ63 his3-Δ200 leu2-Al GAL" with -- *MAT*a *ura3-52 lys2-801$_a$ ade2-101$_o$ trp1-Δ63 his3-Δ200 leu2-Δl GAL* --
Lines 65 and 67, replace "ADE2" with -- *ADE2* --

Column 14
Line 2, replace "BamHI/Bgn1II" with -- *Bam*HI/*Bgl*II --
Lines 2 and 3, replace "NotI" with -- *Not*I --
Lines 10-12, replace "(MATα ura3-52 trp1-Δ63 his3-Δ200 leu2::pGAL10-HO/URA3 GAL)" with -- (*MAT*α *ura3-52 trp1-Δ63 his3-Δ200 leu2::pGAL10-HO/URA3 GAL*) --
Lines 13, 21, 28, 53 and 55 replace "HO" with -- *HO* --
Line 16, replace " "NotI fragment encoding the ADE2 gene" with -- *Not*I fragment encoding the *ADE2* gene --
Line 34, replace "diluted to 1.0 OD600$_{nm}$/ml and serially diluted to $10^{-4}$ at $10.2^{-2}$-increments" with -- diluted to 1.0 OD600$_{nm}$/ml and serially diluted to $10^{-4}$ at $10^{-2}$ increments--
Lines 46-47, replace "(MATa, lys2-801, GAL) and GY5303 (MATα lys2-801$_a$ GAL)" with --(*MAT*a, *lys2-801* α *GAL*) and GY5303 (*MAT*a *lys2-801* α *GAL*)

UNITED STATES PATENT AND TRADEMARK OFFICE
CERTIFICATE OF CORRECTION

PATENT NO. : 6,670,154 B1
DATED : December 30, 2003
INVENTOR(S) : Ronald A. Hitzeman and George E. Chisholm, IV It is certified that error appears in the above-identified patent and that said Letters Patent is hereby corrected as shown below:

Column 14, cont'd.,
Line 54, replace "MATα to MATa" with -- *MAT*α *to MAT*a --
Line 58, replace "Tip⁺" with -- Trp⁺ --
Line 60, replace "GeT774" with -- GET774 --
Line 67, replace "MATα" with -- *MAT*α --

Column 15,
Lines 4, 45 and 47, replace "MATa" with -- *MAT*a --
Lines 5, 6, 56 and 57, replace "HO" with -- *HO* --
Line 48, replace "MATα" with -- *MAT*α --

Column 16,
Line 53, replace "(MATa trp1-Δ63 ura3-52 ade2-101$_o$ his3-Δ200 leu2-Δ1)" with
-- (*MAT*a *trp1-Δ63 ura3-52 ade2-101$_o$ his3-Δ200 leu2-Δ1*) --

Column 17,
Lines 10-11, replace "TRP1 URA3" with -- *TRP*1 *URA*3 --
Line 11, replace "ADE2" with -- *ADE2*--
Lines 12 and 59, replace "HIS3" with -- *HIS*3 --
Lines 12, 65 and 67, replace "HO" with -- *HO* --
Line 34, replace "Ade⁺ and Ad-" with -- Ade⁺ and Ade⁻ --
Line 38, "TRP1" with -- *TRP1* --
Lines 46 and 48, replace "NotI" with -- *Not*I --
Line 51, replace "GET860being" with -- GET860 being --
Line 55, replace "fragment length." with --fragment length (see FIG. 4B). --
Line 57, replace "NotI and BamHI" with -- *Not*I and *Bam*HI --l
Line 61, replace "NotI-BamHl" with -- *Not*I-*Bam*Hl --

Column 18,
Line 1, replace "Example 2" with -- Example 9 --
Lines 2, 5, 8, 10, 13, 22, 23 and 67, replace "HO" with -- *HO* --
Line 11, replace "DNA and were" with -- DNAs were --
Lines 12 and 62, replace "BamHI" with -- *Bam*HI --
Line 35, replace "ADE2" with -- *ADE2* --

Column 19,
Lines 48, 52 and 59, replace "HO" with -- *HO* --

Column 20,
Line 42, 48, 52, 53, 58, 61 and 66 (both occurrences), replace "BamHI" with
-- *Bam*HI --
Lines 48, 49, 53, 55, and 66 replace "NotI" with -- *Not*I --
Lines 50 and 55, replace "NcoI" with -- *Nco*I --

UNITED STATES PATENT AND TRADEMARK OFFICE
CERTIFICATE OF CORRECTION

PATENT NO.    : 6,670,154 B1
DATED         : December 30, 2003
INVENTOR(S)   : Ronald A. Hitzeman and George E. Chisholm, IV It is certified that error appears in the above-identified patent and that said Letters Patent is hereby corrected as shown below:

Column 21,
Line 1, replace "NcoI and NotI" with -- *Nco*I and *Not*I --
Lines 4 and 57, replace "Tetrahymena" with -- *Tetrahymena* --
Lines 17, 48 and 50, replace :KpnI" with -- *Kpn*I --
Lines 20 and 25, replace "in vivo" with -- *in vivo* --
Lines 22, 34, 35, 38, 40, 43, 48 and 52, replace "pyrD" with -- *pyrD* --
Line 28, replace "AMTa HO, AM Tα HO, PI-SceI" with -- *MAT*a *HO*, *MA T*α *HO*, *PI-Sce*I --
Line 29, replace "HIS3)" with -- *HIS3*). --
Lines 30-31, replace "ClaI/SalI" with -- *Cla*I/*Sal*I --
Lines 32, 45, and 51, replace "AatII/NdeI" with -- *Aat*II/*Nde*I --
Line 39, replace "EcoRI/AatII" with -- *Eco*RI/*Aat*II --
Line 41, replace "NdeI/HindIII" with -- *Nde*I/*Hind*III --
Line 44, replace "EcoRI/HindIII" with -- *Eco*RI/*Hind*III --
Line 45, replace "pUCI 18." with -- pUC118. --
Line 50, replace "AatII and NdeI" with -- *Aat*II and *Nde*I --
Lines 58 and 60, replace "XhoI" with -- *Xho*I --

Column 22,
Line 1, replace "KpnI" with -- *Kpn*I --
Lines 4-7, replace

"{F′, endA1, hsdR2(r$_K^-$m$_K^+$), supE44, thi-1, relA?, rfbD1?, spoT1?, mcrB1⁻} and *E. coli* K12 strain NM522 {λ⁻, F′, lacIq Δ(lacZ)M15, proA⁺B⁺/supE, Δ(lac-proAB), thiΔ(hsdMS-mcrB)5" with -- {*F′, endA1, hsdR2(r$_K^-$m$_K^+$), supE44, thi-1, relA?, rfbD1?, spoT1?, mcrb1⁻*} and *E. coli* K12 strain NM522 {λ⁻, *F′, lacIq Δ(lacZ)M15, proA⁺B⁺/supE, Δ(lac-proAB), thiΔ(hsdMS-mcrB)5* --

Lines 10, 12, and 27, replace "pyrD" with -- *pyrD* --
Lines 45-49, replace "(HO endonuclease gene under galactose control, MATα ura3-52 trp1-Δ63 his3-Δ200 leu2::pGAL10 -HO/URA3 GAL) and GY5097 (YPH499=MATa ura3-52 lys2-801$_a$ ade2-101$_o$ trp1-Δ63 his3-Δ200 leu2-Δ1 GAL) have been made rho⁰" with -- (*HO* endonuclease gene under galactose control, *MAT*α *ura3-52 trp1-Δ63 his3-Δ200 leu2*::pGAL10-HO/*URA3 GAL*) and GY5097 (YPH499 = *MAT*a *ura3-52 lys2-801$_a$ ade2-101$_o$ trp1-Δ63 his3-Δ200 leu-Δ1 GAL*) have been made rho° --

Column 23,
Line 2, replace "100 1000 bacteria" with --100-1000 bacteria --
Lines 9 and 11, replace "PI-SceI" with -- PI-*Sce*I --
Lines 14 and 15, replace "HO" with -- *HO* --
Line 18, replace "Ura⁺transformants" with -- Ura⁺ transformants --
Line 26, replace "HIS3" with -- *HIS3* --
Line 45, replace "lys2-801$_a$, ade2-101$_o$, his3-Δ200, leu2-Δ1" with -- *lys2-801$_a$ ade2-101$_o$, his3-Δ200, leu2-Δ1* --
Line 47, replace "Trp⁺ 0and Ura⁺" with -- Trp⁺ and Ura⁺ --
Line 55, replace "microchondrial" with -- mitochondrial --

UNITED STATES PATENT AND TRADEMARK OFFICE
CERTIFICATE OF CORRECTION

PATENT NO. : 6,670,154 B1
DATED : December 30, 2003
INVENTOR(S) : Ronald A. Hitzeman and George E. Chisholm, IV It is certified that error appears in the above-identified patent and that said Letters Patent is hereby corrected as shown below:

Table 1,
Replace "lucine" with -- leucine --

Table 2,
Delete Table 2, and insert therefore
--

TABLE 2
Test of AYAC Linear DNAs

| DNA Form | HO Sites | Total | Red | Sect. | % Red | % Sect. | % R + S | Ave % R + S |
|---|---|---|---|---|---|---|---|---|
| GET860(A) | P | − | 203 | 1 | 4 | 0.49% | 1.97% | 2.46% | |
| GET860(B) | P | − | 254 | 1 | 1 | 0.39% | 0.39% | 0.79% | |
| GET856(A) | P | + | 214 | 1 | 1 | 0.47% | 0.47% | 0.93% | |
| GET856(B) | P | + | 210 | 2 | 0 | 0.95% | 0.00% | 0.95% | |
| GET860(A) | L | − | 183 | 27 | 24 | 14.75% | 13.11% | 27.87% | |
| GET860(B) | L | − | 216 | 22 | 54 | 10.19% | 25.00% | 35.19% | |
| GET856(A) | L | + | 175 | 0 | 2 | 0.00% | 1.14% | 1.14% | |
| GET856(B) | L | + | 154 | 27 | 34 | 17.53% | 22.08% | 39.61% | |
| GET860(A) | L | − | 420 | 76 | 58 | 18.10% | 13.81% | 31.90% | 29.59% |
| " | L | − | 385 | 53 | 52 | 13.77% | 13.51% | 27.27% | |
| GET860(B) | L | − | 570 | 92 | 105 | 16.14% | 18.42% | 34.56% | 36.79% |
| " | L | − | 510 | 87 | 112 | 17.06% | 21.96% | 39.02% | |
| GET856(C) | L | + | 323 | 2 | 4 | 0.62% | 1.24% | 1.86% | 2.77% |
| (GYT3693) | L | + | 380 | 12 | 2 | 3.16% | 0.53% | 3.68% | |
| GET856(D) | L | + | 423 | 0 | 0 | 0.00% | 0.00% | 0.00% | 0.00% |
| " | L | + | 385 | 0 | 0 | 0.00% | 0.00% | 0.00% | |
| GET856(E) | L | + | 340 | 14 | 61 | 4.12% | 17.94% | 22.06% | 19.96% |
| " | L | + | 336 | 12 | 48 | 3.57% | 14.29% | 17.86% | |
| GET856(F) | L | + | 298 | 0 | 0 | 0.00% | 0.00% | 0.00% | 0.00% |
| " | L | + | 249 | 0 | 0 | 0.00% | 0.00% | 0.00% | |
| GET856(G) | L | + | 420 | 68 | 79 | 16.19% | 18.81% | 35.00% | 33.92% |
| " | L | + | 469 | 79 | 75 | 16.84% | 15.99% | 32.84% | |
| GET856(H) | L | + | 274 | 1 | 0 | 0.36% | 0.00% | 0.36% | 0.31% |
| " | L | + | 393 | 1 | 0 | 0.25% | 0.00% | 0.25% | |
| GET860(C) | L | − | 698 | 69 | 71 | 9.89% | 10.17% | 20.06% | 19.05% |
| " | L | − | 937 | 47 | 122 | 5.02% | 13.02% | 18.04% | |
| GET860(D) | L | − | 423 | 60 | 78 | 14.18% | 18.44% | 32.62% | 30.56% |
| " | L | − | 386 | 72 | 38 | 18.65% | 9.84% | 28.50% | |
| GET860(G) | L | − | 482 | 72 | 68 | 14.94% | 14.11% | 29.05% | 28.91% |
| " | L | − | 476 | 73 | 64 | 15.34% | 13.45% | 28.78% | |
| GET856(G) | L | + | 380 | 63 | 94 | 16.58% | 24.74% | 41.32% | 43.26% |
| (GYT3695) | L | + | 365 | 80 | 85 | 21.92% | 23.29% | 45.21% | |

Yeast Strain GYS345
Red = Ade⁻ colony,
Sect. = Sectored Colony (Red Ade⁻ and White Ade⁺)
Form P = Plasmid,
L = Linear

--

Signed and Sealed this

Twenty-eighth Day of September, 2004

JON W. DUDAS
*Director of the United States Patent and Trademark Office*

UNITED STATES PATENT AND TRADEMARK OFFICE
CERTIFICATE OF CORRECTION

PATENT NO.    : 6,670,154 B1
DATED         : December 30, 2003
INVENTOR(S)   : Hitzeman et al.

It is certified that error appears in the above-identified patent and that said Letters Patent is hereby corrected as shown below:

Column 2,
Line 24, please replace "*3*' region" with -- 3' region --
Line 39, please replace "Bg/II" with -- *Bg*/II --

Column 4,
Line 16, please replace "Tetrahymena" with -- *Tetrahymena* --

Column 11,
Line 23, please replace "Φ80δ1acZΔM15" with -- *Φ80δ1acZΔM15* --
Line 50, please replace "Strain S 1799D" with -- Strain S1799D --

Column 14,
Lines 10-12, please replace "(*MATa ura3-52 trp1-Δ63 his3-Δ200 leu2::p*GAL*10-HO/ URA3 GAL*)" with -- (*MATa ura3-52 trp1-Δ63 his3- Δ200 leu2::p*GAL10-HO/ UR*A3 GAL*) --
Line 34, please replace "diluted to 1.0 OD600$_{nm}$/ml and serially diluted to $10^{-4}$ at $10^{-2}$increments" with -- diluted to 1.0 OD600$_{nm}$/ml and serially diluted to $10^{-4}$ at $10^{-2}$ increments --
Lines 46-47, please replace "(*MATa, lys*2-801 α *GAL*) and GY5303 (*MATa lys*2-801 α *GAL*)" with -- (*MATa, lys*2-801$_α$ *GAL*) and GY5303 (*MATa lys*2-801$_a$ *GAL*) --

Column 17,
Line 57, please replace "N*ot*I and B*am*HI -1" with -- N*ot*I and B*am*HI --

UNITED STATES PATENT AND TRADEMARK OFFICE
CERTIFICATE OF CORRECTION

PATENT NO. : 6,670,154 B1
DATED : December 30, 2003
INVENTOR(S) : Hitzeman et al.

It is certified that error appears in the above-identified patent and that said Letters Patent is hereby corrected as shown below:

Column 21,
Line 28, please replace "*MAT*a *HO, MA T*α *HO, PI-Sce*I" with -- *MAT*a *HO, MAT*α *HO, PI-Sce*I --
Lines 32, 45 and 51, please replace "A*at*II1*Nde*I" with -- A*at*II/*Nde*I --

Signed and Sealed this

Twenty-first Day of June, 2005

JON W. DUDAS
*Director of the United States Patent and Trademark Office*